(12) United States Patent
Fields et al.

(10) Patent No.: US 11,925,733 B2
(45) Date of Patent: Mar. 12, 2024

(54) MALODOR COUNTERACTANT COMPOSITION AND METHODS

(71) Applicant: Bell Flavors & Fragrances, Inc., Northbrook, IL (US)

(72) Inventors: Marvel Fields, Northbrook, IL (US); Richard Nero, Gurnee, IL (US); Steve Orson, Arlington Heights, IL (US); Robert Siegel, Chicago, IL (US); John Kocis, Arlington Heights, IL (US)

(73) Assignee: Bell Flavors & Fragrances, Inc., Northbrook, IL (US)

( * ) Notice: Subject to any disclaimer, the term of this patent is extended or adjusted under 35 U.S.C. 154(b) by 882 days.

(21) Appl. No.: 16/341,558

(22) PCT Filed: Nov. 20, 2017

(86) PCT No.: PCT/US2017/062509
§ 371 (c)(1),
(2) Date: Apr. 12, 2019

(87) PCT Pub. No.: WO2018/094314
PCT Pub. Date: May 24, 2018

(65) Prior Publication Data
US 2021/0353814 A1     Nov. 18, 2021

Related U.S. Application Data

(60) Provisional application No. 62/424,975, filed on Nov. 21, 2016.

(51) Int. Cl.
*A61L 9/04* (2006.01)
*A61K 8/27* (2006.01)
(Continued)

(52) U.S. Cl.
CPC ........ *A61L 9/04* (2013.01); *A61K 8/27* (2013.01); *A61K 8/31* (2013.01); *A61K 8/33* (2013.01);
(Continued)

(58) Field of Classification Search
CPC ... A61K 8/34; A61K 8/31; A61K 8/27; A61K 8/33; A61K 8/361; A61K 8/37;
(Continued)

(56) References Cited

U.S. PATENT DOCUMENTS

| 8,357,359 B2 | 1/2013 | Woo et al. |
| 9,226,641 B2 | 1/2016 | Woo et al. |

(Continued)

FOREIGN PATENT DOCUMENTS

| WO | WO 2016/049523 A1 | 3/2016 | |
| WO | WO 2016/146671 A1 | 9/2016 | |
| WO | WO-2016146671 A1 * | 9/2016 | ............. A61L 9/012 |

*Primary Examiner* — Jianfeng Song
(74) *Attorney, Agent, or Firm* — Jenei LLC

(57) ABSTRACT

The present invention relates to compositions and methods for malodor reduction. The malodor control compositions are suitable for use in a variety of applications, including use in consumer products, for example, air freshening compositions, laundry detergents, fabric enhancers, surface cleaners, beauty care products, dish care products, diapers, feminine protection articles, animal and pet litter compositions and plastic films for garbage bags. Such malodor control technologies do not unduly interfere with the scent of the perfumed or unperfumed situs that is treated with the malodor control technology.

11 Claims, 4 Drawing Sheets

Odorant Only

(51) Int. Cl.
  *A61K 8/31* (2006.01)
  *A61K 8/33* (2006.01)
  *A61K 8/34* (2006.01)
  *A61K 8/36* (2006.01)
  *A61K 8/37* (2006.01)
  *A61L 9/014* (2006.01)
  *A61L 15/20* (2006.01)
  *A61L 15/46* (2006.01)
  *A61Q 15/00* (2006.01)

(52) U.S. Cl.
  CPC .............. *A61K 8/34* (2013.01); *A61K 8/361* (2013.01); *A61K 8/37* (2013.01); *A61L 9/014* (2013.01); *A61L 15/20* (2013.01); *A61L 15/46* (2013.01); *A61Q 15/00* (2013.01); *A61L 2209/21* (2013.01)

(58) Field of Classification Search
  CPC ........ A61L 2209/21; A61L 15/46; A61L 9/14; A61L 9/04; A61L 9/014; A61L 15/20; A61L 9/012; A61Q 15/00; A61Q 13/00; A61F 13/8405
  See application file for complete search history.

(56) References Cited

U.S. PATENT DOCUMENTS

| | | | |
|---|---|---|---|
| 9,642,927 | B2 | 5/2017 | Hollingshead et al. |
| 9,655,792 | B2 | 5/2017 | Woo et al. |
| 9,714,401 | B2 | 7/2017 | Frankenbach |
| 10,552,557 | B2 | 2/2020 | Frankenbach et al. |
| 2008/0249490 | A1 | 10/2008 | Carlucci et al. |
| 2012/0269758 | A1* | 10/2012 | Cornwell .................. A61Q 5/12 132/203 |
| 2012/0301421 | A1* | 11/2012 | Hecking ................... A61L 9/14 424/76.8 |
| 2013/0165532 | A1 | 6/2013 | Narula et al. |
| 2013/0266642 | A1 | 10/2013 | Hollingshead et al. |
| 2013/0336914 | A1 | 12/2013 | Horenziak et al. |
| 2016/0129144 | A1 | 5/2016 | Woo et al. |
| 2018/0326107 | A9 | 11/2018 | Woo et al. |
| 2019/0008991 | A1 | 1/2019 | Horenziak et al. |

* cited by examiner

MALODOR COUNTERACTANT COMPOSITION AND METHODS

CROSS-REFERENCE TO RELATED APPLICATIONS

This application claims the benefit of priority under 35 U.S.C. § 119(e) to U.S. Provisional Application Ser. No. 62/424,975, entitled "MALODOR COUNTERACTANT COMPOSITION AND METHODS," [Docket 1022.210PRV] filed Nov. 21, 2016, the contents of which are incorporated herein by reference in their entirety.

BACKGROUND OF THE INVENTION

1. Field of the Invention

The present invention relates to malodor counteractant compositions and methods for using them. The present invention also relates to low odor threshold fragrance materials that match the volatility of malodor molecules of urine, sweat, feces and pet odors, which effectively block their malodor.

2. Description of the Related Art

The use of disposable diapers and absorbent catamenial tissues is growing rapidly worldwide because of an aging global population. Absorbency and odor control are the two key properties of these products. There have been many advances in diaper technology and catamenial design addressing absorbency and odor control such as: high fluid absorbency gels, twined fibers directing flow, fiber modifications, micro-encapsulated scents, inclusion of inorganic salts, zeolites, antibacterial agents, organic acids, detergents to speed fluid distribution, odor neutralizing chemicals, and strong fragrances to mask odors. Unpleasant body odors are mainly organic molecules such as amines, acids, alcohols, carboxylic acids, aldehydes, ketones, phenolics, and sulfur compounds such as, thiols, mercaptans, and sulfides.

Rogers, Warren and Qi in U.S. Patent 2003/0089885 A1 identify carboxylic acids including propionic acid (foot malodor) hexanoic acid (pet malodor), isovaleric acid and 3-methyl-2-hexenoic acid as components of underarm malodor. The '885 reference describes low molecular weight acetals, O-acrylated alcohols and esters help block these odors. These carboxylic acids are strong contributors to human and pet generated odors, but odor control needed improvement.

Although these developments have greatly enhanced the performance of these products, odor control is still a challenge, as the wearer's of these products do not want a sudden release of a scent or malodor itself when leakage occurs. The objective is to block all odors from escaping without releasing a secondary scent, which may take a combination of technologies.

Procter & Gamble U.S. Pat. No. 5,861,144A describes absorbent betacyclodextrin molecules with encapsulated and free fragrance mixtures using some low odor threshold materials.

Procter & Gamble US 201137169 A2 describes using two or more reactive organic aldehydes reacting with organic acids like benzoic acid to neutralize odors. The betacyclodextrin effectively absorbs some odors, but reactive organic aldehydes impart a fatty odor from the aldehydes.

Procter & Gamble U.S. Pat. No. 5,733,272A describes odor release technology releasing a scent when wetted to signal the need to change a diaper with micro encapsulated fragrances. It also teaches us the use of gelling agents to impart super absorbency of fluids and retain some of the odor in the gel's matrix. Again the objective is not to release any odors signaling diaper wetting by wearer.

Giovanni Carlucci US20080249490 uses silica gels and zeolite to partially absorb odors, but highly odiferous fragrance materials to block odors. Some fragrance materials render the nose anosmic and unable to smell other odors, like benzaldehyde in men's urinal blocks, but strong odors are contrary to today's market needs.

Procter & Gamble WO 1998007405 A1 describes high molecular weight keto-esters formed by reacting B Ketones and alkali ethoxylates releasing two or more smaller molecular weight fragrance materials giving a sustained lasting perfume retention. Releasing scents is highly desirable in the detergent, fabric softener and some personal products but not always in adult diapers.

Calwood Chemical WO 1998053784 use Antimony Pentoxide, Zirconium Hydroxide and Zirconium Sulfate to control odors in diapers.

Ceca S. A. U.S. Pat. No. 6,277,772B1 use of Silver ions and Zeolites. They are expensive and OSHA Personal Exposure limits are very low. Zirconium found in antiperspirants cause granulomata on human skin. Exposure to Antimony also causes skin irritation.

The present invention now identifies a specific fragrance formula of low odor threshold materials that match the volatility of malodors from human, pet, and body odors and combine with them to block odors while releasing little or no accompanying scent or perfume at very low concentration.

SUMMARY OF THE INVENTION

A composition comprising a malodor reduction material is disclosed. The present invention relates to malodor counteractant compositions and methods for using them.

The malodor control composition comprises a Malodor Counteractant (MOC) formula that includes a mixture of materials designed to deliver genuine malodor neutralization and not function merely by covering up or masking odors. Malodor neutralization provides a sensory and analytically measurable (e.g. gas chromatograph) malodor reduction. Thus, if the malodor control composition delivers genuine malodor neutralization, the composition will reduce malodors in the vapor and/or liquid phase.

As the diaper market is growing rapidly, it will require an intimate knowledge of how perfumes act on malodors in diapers. In extensive perfume raw material studies of individual perfume ingredients against urine malodor of the present invention, how each ingredient worked with or against the malodor was measured. Materials that successfully covered or blocked the malodor were then divided into two categories. Category One are ingredients that reduced or eliminated the urine malodor with little or no odor of their own (low odor threshold), and Category 2 are those ingredients that reduced or eliminated the urine malodor but had a high or medium odor threshold. With the surprising success of the Malodor Counteractant (MOC) formula of the present invention and the synergistic effect against odors, it was successfully tested against sweat odor, body odor, fecal odor, pet odor, foot odor, household food odors, and garbage and blood odor.

In one or more embodiments, the present invention provides for a Malodor Counteractant (MOC) formula consisting of a mixture of the following ingredients:

1. Applelide (also known as: Applelide (IFF) (CAS #478695-70-4); 3-(3,3-dimethylcyclohexyl)-2-ethoxycarbonyl-butanoic acid; 1-(3-3 dimethylcyclohexyl) ethylpropanedioic acid; propanedioic acid 1-(3,3-dimethylcyclohexyl)ethyl ethyl ester
2. Diphenyl oxide (CAS #101-84-8); (also known as: Oxydibenzene, diphenyl ether, phenoxybenzene and 1,1'-oxibisbenzene);
3. Apo Patchone: also known as Apo Patchone Coeur (IFF) or Folrosia (CAS #4621-04-9); (also know as: butyl-4-tert cyclohexanol, or PTBCH Alcohol, 4-isopropyl cyclohexanol (cis & trans)); and
4. Phenirat®: IUPAC Name: 2-Phenoxyethyl-2-methylpropanoate (CAS #103-60-6); (also known as floranol, 2-phenoxyethylisobutyrate or 2-methylpropanoic acid 2-phenoxyethyl ester);

wherein each compound in present in an amount from 0.5% to 60% (% wt.).

In one or more embodiments, the present invention provides for a Malodor Counteractant (MOC) formula comprising 1-(3-3 dimethylcyclohexyl)ethylpropanedioic acid ethyl ester, diphenyl oxide, 4-(methylethyl)cyclohexan-1-ol, and 2-methylpropanoic acid 2-phenoxyethyl ester; wherein each compound in present in an amount from 0.5% to 60% (% wt.); and wherein the composition is capable of neutralizing urine odors, sweat odors, and pet odors and wherein the ingredients work synergistically as a malodor counteractant compound.

In one or more embodiments, the present invention provides for a Malodor Counteractant (MOC) formula comprising 1-(3-3 dimethylcyclohexyl)ethylpropanedioic acid ethyl ester, diphenyl oxide, 4-(methylethyl)cyclohexan-1-ol, and 2-methylpropanoic acid 2-phenoxyethyl ester; wherein at least a portion of one or more compound is complexed or encapsulated.

In one or more embodiments, the Malodor Counteractant (MOC) compositions of the present invention comprise microcapsules containing the active materials and/or an optional odor control agents. It should be understood that the encapsulated agents need not be completely encapsulated (that is, in some embodiments, it may be partially encapsulated). The same is true for the microcapsules containing the active materials. There are a non-limiting number of embodiments of the compositions described herein. These embodiments include, but are not limited to embodiments in which at least some of the same microcapsules contain both an active material and the optional odor control agent therein. In other embodiments, the composition may comprise a group of microcapsules that contain an active material, and different microcapsules that contain the optional odor control agent. The composition may comprise microcapsules with different types of shells or coating materials. In addition, in some embodiments, the encapsulated odor control agent and the odor control agent outside of the microcapsules may be the same odor control agent. In other embodiments, they may be different odor control agents.

The present compositions can also contain a wide variety of additional optional ingredients such as dispersants, solvents, aerosol propellants, surfactants, free perfume, antimicrobial actives/preservatives, wrinkle control agents, and the like. The compositions can be used to reduce or remove malodor from surfaces (such as fabrics) and provide a controlled-release of the active material.

In one or more embodiments, the malodor control composition comprises (a) from 1 to 25 wt. % Applelide; (b) from 1 to 25 wt. % Diphenyl oxide; (c) from 1 to 25 wt. % Apo Patchone; and (d) from 5 to 90 wt. % Phenirat.

In another embodiment, the malodor control composition comprises (a) from 2 to 20 wt. % Applelide; (b) from 2 to 20 wt. % Diphenyl oxide; (c) from 2 to 20 wt. % Apo Patchone; and (d) from 10-90 wt. % Phenirat.

In another embodiment, the malodor control composition comprises (a) from 2 to 20 wt. % Applelide; (b) from 2 to 20 wt. % Diphenyl oxide; (c) from 2 to 20 wt. % Apo Patchone; and (d) from 20-80 wt. % Phenirat.

In another embodiment, the malodor control composition comprises (a) from 5-15 wt. % Applelide; (b) from 5-15 wt. % Diphenyl oxide; (c) from 5-15 wt. % Apo Patchone; and (d) from 30-70 wt. % Phenirat.

In another embodiment, the malodor control composition comprises (a) from 5-15 wt. % Applelide; (b) from 5-15 wt. % Diphenyl oxide; (c) from 5-15 wt. % Apo Patchone; and (d) from 30-60 wt. % Phenirat.

In one or more embodiments, the malodor control composition comprises (a) at least 5 wt. % Applelide; (b) at least 5 wt. % Diphenyl oxide; (c) at least 5 wt. % Apo Patchone; and (d) at least 5 wt. % Phenirat. In another embodiment, the composition comprises at least 5, 6, 7, 8, 9, 10, 11, 12, 13, 14, 15, 16, 17, 18, 19, 20 wt. % or more of Applelide. In another embodiment, the composition comprises at least 5, 6, 7, 8, 9, 10, 11, 12, 13, 14, 15, 16, 17, 18, 19, 20 wt. % or more of Diphenyl oxide. In another embodiment, the composition comprises at least 5, 6, 7, 8, 9, 10, 11, 12, 13, 14, 15, 16, 17, 18, 19, 20 wt. % or more of Apo Patchone. In another embodiment, the composition comprises at least 5, 10, 15, 20, 25, 30, 35, 40 wt. % or more of Phenirat.

In another embodiment, the composition comprises at most 5, 10, 15, 20, 25, 30, 35, 40, 45, 50, 55, 60, 65, 70, 75, 80 wt. % or less of Applelide. In another embodiment, the composition comprises at most 5, 10, 15, 20, 25, 30, 35, 40, 45, 50, 55, 60, 65, 70, 75, 80 wt. % or less of Diphenyl oxide. In another embodiment, the composition comprises at most 5, 10, 15, 20, 25, 30, 35, 40, 45, 50, 55, 60, 65, 70, 75, 80 wt. % or less of Apo Patchone. In another embodiment, the composition comprises at most 15, 20, 25, 30, 35, 40, 45, 50, 55, 60, 65, 70, 75, 80, 85, 90 wt. % or less of Phenirat.

In one aspect, the malodor reduction composition's mixture is present in a final composition in an amount up to 100%, by weight of the malodor reduction composition, alternatively from about 5% to about 100%, alternatively from about 10% to about 100%, alternatively from about 30% to about 100%, alternatively from about 50% to about 100%, alternatively from about 70% to about 100%, alternatively from about 80% to about 100%, alternatively from about 0.01% to about 95%, alternatively from about 0.01% to about 85%, alternatively from about 0.01% to about 75%, alternatively from about 0.01% to about 65%, alternatively from about 0.01% to about 55%, alternatively from about 0.01% to about 45%, alternatively from about 0.01% to about 35%, alternatively from about 0.01% to about 25%, alternatively from about 0.1% to about 15%, alternatively from about 0.001% to about 10%, alternatively from about 0.001% to about 5%, alternatively from about 0.001% to about 5%, alternatively from about 0.001% to about 3%, alternatively from about 0.001% to about 1%, alternatively about 0.001% to about 0.5%, by weight of the malodor reduction composition.

A blend of these low odor threshold malodor counteractant (MOC) materials each contributes to odor blocking, but none by themselves eliminate the malodor as effectively as the combination wherein the combination acts synergistically. A combination of these selected materials included in the present invention can provide odor control for diaper, catamenial products, body deodorants, cat litter products, and household products. In diaper products they can alleviate consumers' fear of being discovered by sudden odor surges, when sudden urine or feces leakage enters into the substrate, by providing malodor blocking without subsequent release of perfume scent. In cat litter use, the malodor counteractant materials of the present invention can control odors without releasing overpowering scents that may be obnoxious to consumers. In antiperspirants, the malodor counteractant (MOC) materials can block body odors.

These and other features are explained more fully in the embodiments illustrated below. It should be understood that in general the features of one embodiment also may be used in combination with features of another embodiment and that the embodiments are not intended to limit the scope of the invention.

BRIEF DESCRIPTION OF THE DRAWINGS

The various exemplary embodiments of the present invention, which will become more apparent as the description proceeds, are described in the following detailed description in conjunction with the accompanying drawings, in which.

DETAILED DESCRIPTION

Definitions

Figure 1:
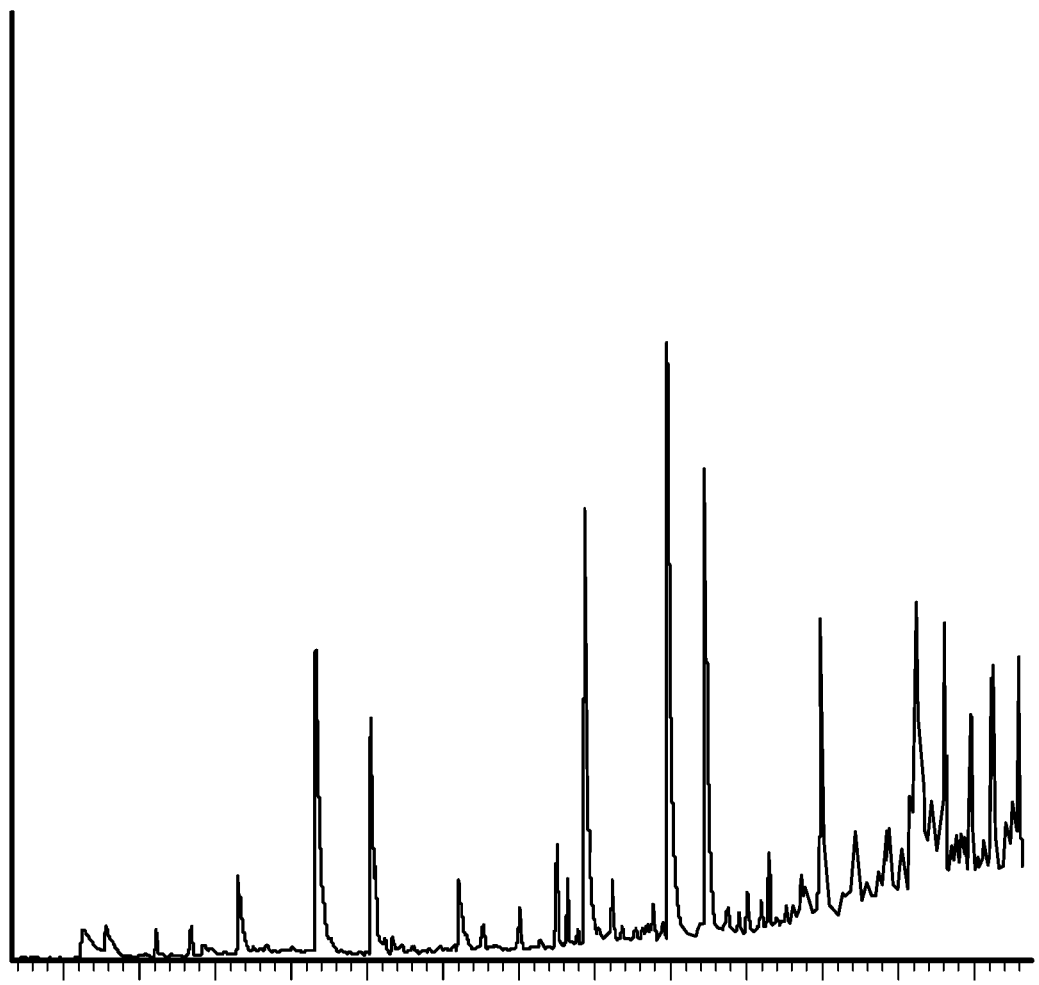
FIG. 1 illustrates gas chromatographic analyses showing products eluted from the odorant alone with carvyl acetate added as a marker.

"Absorbent article" refers to materials that absorb and contain body exudates, such as urine, menses, and feces. The term "disposable" is used herein to describe absorbent articles, which are not intended to be laundered or otherwise restored or reused as an absorbent article after a single use. Examples of absorbent articles include diapers, toddler training pants, adult incontinence garments, and feminine hygiene garments such as sanitary napkins, pantiliners, urine pads, interlabial devices, hemorrhoid pads, and the like.

As used herein "consumer product" means baby care, beauty care, fabric & home care, family care, feminine care, and/or health care products or devices. Such products include but are not limited to plastic films garbage bags, storage bags, storage wraps, diapers, bibs, wipes, garments, textiles including sheets and towels, composters; products for and/or methods relating to treating hair (human, dog, and/or cat), including, conditioning, wet or dry shampooing, styling, scalp treatments; deodorants and antiperspirants; personal cleansing; cosmetics; skin care including application of creams, lotions, fine fragrances and other topically applied products for consumer use; and shaving products, products for and/or methods relating to treating fabrics, hard surfaces and any other surfaces in the area of fabric and home care, including: air care including air filtration, car care, dishwashing, fabric conditioning (including softening), laundry detergency, laundry and rinse additive and/or care, hard surface cleaning and/or treatment, towel bowl cleaners and other cleaning and/or malodor treatments for consumer, agricultural, industrial or institutional use; products and/or methods relating to bath tissue, facial tissue, paper handkerchiefs, and/or paper towels; tampons, feminine napkins; and related products and/or methods.

The terms "fragrance formulation", "fragrance composition", and "perfume composition" mean the same and refer to a consumer composition that is a mixture of materials including, for example, alcohols, aldehydes, ketones, esters, ethers, lactones, nitriles, natural oils, synthetic oils, and mercaptans, which are admixed so that the combined odors of the individual components produce a pleasant or desired fragrance.

The term "fragrance product" means a consumer product containing a fragrance ingredient that adds fragrance or masks malodor. Fragrance products may include, for example, perfumes, colognes, bar soaps, liquid soaps, shower gels, foam baths, cosmetics, skin care products such as creams, lotions and shaving products, hair care products for shampooing, rinsing, conditioning, and styling, deodorants and antiperspirants, feminine care products such as tampons and feminine napkins, baby care products such as diapers, bibs and wipes, family care products such as bath tissues, facial tissues, paper handkerchiefs or paper towels, fabric care products such as detergents, fabric softeners and fabric fresheners, air care products such as air fresheners and fragrance delivery systems, cosmetic preparations, cleaning agents and disinfectants such as detergents, dishwashing materials, scrubbing compositions, glass and metal cleaners such as window cleaners, countertop cleaners, floor and carpet cleaners, toilet cleaners and bleach additives, washing agents such as all-purpose, heavy duty, and hand washing or fine fabric washing agents including laundry detergents and rinse additives. The fragrance product of the present invention is a consumer product that contains a compound of the present invention. The fragrance product of the present invention may contain a compound of the present invention and further a complementary fragrance compound as defined above.

The term "improving" in the phrase "improving, enhancing or modifying a fragrance formulation" is understood to mean raising the fragrance formulation to a more desirable character. The term "enhancing" is understood to mean making the fragrance formulation greater in effectiveness or providing the fragrance formulation with an improved character. The term "modifying" is understood to mean providing the fragrance formulation with a change in character.

As used herein, "malodor" refers to compounds generally offensive or unpleasant to most people, such as the complex odors associated with urine, sweat, body odor, foot odor or bowel movements.

As used herein, "neutralize" or "neutralization" refers to the ability of a compound or product to reduce or block malodorous compounds. Odor neutralization may be partial, affecting only some of the malodorous compounds in a given context, or affecting only part of a malodorous compound. A malodorous compound may be neutralized by chemical reaction resulting in a new chemical entity, by sequestration, by chelation, by association, or by any other interaction rendering the malodorous compound less malodorous or non-malodorous.

As used herein, "odor blocking" refers to the ability of a compound to combine with the malodor rendering little or no odor detected.

As used herein, "odor masking" refers to the ability of a compound with a non-offensive or pleasant smell that is dosed such that it limits the ability to sense a malodorous compound. Odor-masking may involve the selection of compounds, which coordinate with an anticipated malodor to change the perception of the overall scent provided by the combination of odorous compounds.

The term "olfactory acceptable amount" is understood to mean the amount of a compound in a fragrance formulation, wherein the compound will contribute its individual olfactory characteristics. However, the olfactory effect of the fragrance formulation will be the sum of effect of each of the fragrance ingredients. Thus, the compounds of the present invention can be used to improve or enhance the aroma characteristics of the fragrance formulation, or by modifying the olfactory reaction contributed by other ingredients in the formulation. The olfactory acceptable amount may vary depending on many factors including other ingredients, their relative amounts and the olfactory effect that is desired.

Exemplary Embodiments of the Invention

A composition comprising a malodor reduction material is disclosed. The present invention relates to malodor counteractant compositions and methods for using them.

A blend of these low odor threshold malodor counteractant (MOC) materials each contributes to odor blocking, but none by themselves eliminate the malodor as effectively as the combination.

The malodor control composition comprises a Malodor Counteractant (MOC) formula that includes a mixture of compounds designed to deliver genuine malodor neutralization and not function merely by covering up or masking odors. Malodor neutralization provides a sensory and analytically measurable (e.g. gas chromatograph) malodor reduction. Thus, if the malodor control composition delivers a genuine malodor neutralization, the composition will reduce malodors in the vapor and/or liquid phase.

In one or more embodiments, the present invention provides for a Malodor Counteractant (MOC) formula consisting of a mixture of the following ingredients:
1. Applelide (also known as: Applelide® (IFF) (CAS #478695-70-4); 3-(3,3-dimethylcyclohexyl)-2-ethoxycarbonyl-butanoic acid; 1-(3-3 dimethylcyclohexyl) ethylpropanedioic acid; propanedioic acid 1-(3,3-dimethylcyclohexyl)ethyl ethyl ester
2. Diphenyl oxide (CAS #101-84-8); (also known as: Oxydibenzene, diphenyl ether, phenoxybenzene and 1,1'-oxibisbenzene);
3. Apo Patchone: also known as Apo Patchone Coeur (IFF) or Folrosia (CAS #4621-04-9); (also know as: butyl-4-tert cyclohexanol, or PTBCH Alcohol, 4-isopropyl cyclohexanol (cis & trans)); and
4. Phenirat®: IUPAC Name: 2-Phenoxyethyl-2-methyl-propanoate (CAS #103-60-6); (also known as floranol, 2-phenoxyethylisobutyrate or 2-methylpropanoic acid 2-phenoxyethyl ester).

In one or more embodiments, the present invention provides for a Malodor Counteractant (MOC) formula comprising 1-(3-3 dimethylcyclohexyl)ethylpropanedioic acid ethyl ester, diphenyl oxide, 4-(methylethyl)cyclohexan-1-ol, and 2-methylpropanoic acid 2-phenoxyethyl ester; wherein each compound in present in an amount from 0.5% to 80% (% wt.); and wherein the composition is capable of neutralizing urine odors, sweat odors, and pet odors and wherein the ingredients work synergistically as a malodor counteractant compound.

In one or more embodiments, the present invention provides for a Malodor Counteractant (MOC) formula comprising 1-(3-3 dimethylcyclohexyl)ethylpropanedioic acid ethyl ester, diphenyl oxide, 4-(methylethyl)cyclohexan-1-ol, and 2-methylpropanoic acid 2-phenoxyethyl ester; wherein at least a portion of one or more compound is complexed or encapsulated.

In one or more embodiments, the Malodor Counteractant (MOC) compositions of the present invention comprise microcapsules containing the active materials and/or an optional odor control agents. It should be understood that the encapsulated agents need not be completely encapsulated (that is, in some embodiments, it may be partially encapsulated). The same is true for the microcapsules containing the active materials. There are a non-limiting number of embodiments of the compositions described herein. These embodiments include, but are not limited to embodiments in which at least some of the same microcapsules contain both an active material and the optional odor control agent therein. In other embodiments, the composition may comprise a group of microcapsules that contain an active material, and different microcapsules that contain the optional odor control agent. The composition may comprise microcapsules with different types of shells or coating materials. In addition, in some embodiments, the encapsulated odor control agent and the odor control agent outside of the microcapsules may be the same odor control agent. In other embodiments, they may be different odor control agents.

The present compositions can also contain a wide variety of additional optional ingredients such as dispersants, solvents, aerosol propellants, surfactants, free perfume, antimicrobial actives/preservatives, wrinkle control agents, and the like. The compositions can be used to reduce or remove malodor from surfaces (such as fabrics) and provide a controlled-release of the active material.

In one or more embodiments, the malodor control formula or composition comprises (a) from 1 to 35 wt. % Applelide; (b) from 1 to 35 wt. % Diphenyl oxide; (c) from 1 to 35 wt. % Apo Patchone; and (d) from 5 to 90 wt. % Phenirat.

In one or more embodiments, the malodor control composition comprises (a) from 2 to 30 wt. % Applelide; (b) from 2 to 30 wt. % Diphenyl oxide; (c) from 2 to 30 wt. % Apo Patchone; and (d) from 5 to 80 wt. % Phenirat.

In one or more embodiments, the malodor control composition comprises (a) from 2 to 25 wt. % Applelide; (b)

from 2 to 25 wt. % Diphenyl oxide; (c) from 2 to 25 wt. % Apo Patchone; and (d) from 5 to 75 wt. % Phenirat.

In another embodiment, the malodor control composition comprises (a) from 2 to 20 wt. % Applelide; (b) from 2 to 20 wt. % Diphenyl oxide; (c) from 2 to 20 wt. % Apo Patchone; and (d) from 10-90 wt. % Phenirat.

In another embodiment, the malodor control composition comprises (a) from 2 to 20 wt. % Applelide; (b) from 2 to 20 wt. % Diphenyl oxide; (c) from 2 to 20 wt. % Apo Patchone; and (d) from 20-80 wt. % Phenirat.

In another embodiment, the malodor control composition comprises (a) from 5-15 wt. % Applelide; (b) from 5-15 wt. % Diphenyl oxide; (c) from 5-15 wt. % Apo Patchone; and (d) from 30-70 wt. % Phenirat.

In another embodiment, the malodor control composition comprises (a) from 5-15 wt. % Applelide; (b) from 5-15 wt. % Diphenyl oxide; (c) from 5-15 wt. % Apo Patchone; and (d) from 30-60 wt. % Phenirat.

In one or more embodiments, the malodor control composition comprises (a) at least 2 wt. % Applelide; (b) at least 2 wt. % Diphenyl oxide; (c) at least 2 wt. % Apo Patchone; and (d) at least 5 wt. % Phenirat.

In one or more embodiments, the malodor control composition comprises (a) at least 5 wt. % Applelide; (b) at least 5 wt. % Diphenyl oxide; (c) at least 5 wt. % Apo Patchone; and (d) at least 10 wt. % Phenirat.

In one or more embodiments, the malodor control composition comprises (a) at least 10 wt. % Applelide; (b) at least 10 wt. % Diphenyl oxide; (c) at least 10 wt. % Apo Patchone; and (d) at least 20 wt. % Phenirat.

In one or more embodiments, the malodor control composition comprises (a) at least 15 wt. % Applelide; (b) at least 15 wt. % Diphenyl oxide; (c) at least 15 wt. % Apo Patchone; and (d) at least 30 wt. % Phenirat.

In one or more embodiments, the malodor control composition comprises (a) at least 20 wt. % Applelide; (b) at least 20 wt. % Diphenyl oxide; (c) at least 20 wt. % Apo Patchone; and (d) at least 40 wt. % Phenirat.

In another embodiment, the composition comprises at least 5, 6, 7, 8, 9, 10, 11, 12, 13, 14, 15, 16, 17, 18, 19, 20 wt. % or more of Applelide. In another embodiment, the composition comprises at least 5, 6, 7, 8, 9, 10, 11, 12, 13, 14, 15, 16, 17, 18, 19, 20 wt. % or more of Diphenyl oxide. In another embodiment, the composition comprises at least 5, 6, 7, 8, 9, 10, 11, 12, 13, 14, 15, 16, 17, 18, 19, 20 wt. % or more of Apo Patchone. In another embodiment, the composition comprises at least 5, 10, 15, 20, 25, 30, 35, 40, 45 wt. % or more of Phenirat.

In another embodiment, the composition comprises at most 5, 10, 15, 20, 25, 30, 35, 40, 45, 50, 55, 60, 65, 70, 75, 80 wt. % or less of Applelide. In another embodiment, the composition comprises at most 5, 10, 15, 20, 25, 30, 35, 40, 45, 50, 55, 60, 65, 70, 75, 80 wt. % or less of Diphenyl oxide. In another embodiment, the composition comprises at most 5, 10, 15, 20, 25, 30, 35, 40, 45, 50, 55, 60, 65, 70, 75, 80 wt. % or less of Apo Patchone. In another embodiment, the composition comprises at most 15, 20, 25, 30, 35, 40, 45, 50, 55, 60, 65, 70, 75, 80, 85, 90 wt. % or less of Phenirat.

In one or more embodiments, the present invention provides for a Malodor Counteractant (MOC) formula comprising 1-(3-3 dimethylcyclohexyl)ethylpropanedioic acid ethyl ester, diphenyl oxide, 4-(methylethyl)cyclohexan-1-ol, and 2-methylpropanoic acid 2-phenoxyethyl ester; wherein the formula described herein further comprises one or more additional compounds selected from the group consisting of: 2-phenoxyethanol (CAS #122-99-6), ethyl 10-undecenoate (CAS #692-86-4), 2-methylundecanal (also Aldehyde C-12; MNA) (CAS #110-41-8), Cyclacet® (3a,4,5,6,7,7a-hexahydro-4,7-methano-1h-inden-5(or 6)-yl acetate) (CAS #54830-99-8), and hexyl salicylate (CAS #6259-76-3).

In one or more embodiments, the present invention provides for a Malodor Counteractant (MOC) formula comprising 1-(3-3 dimethylcyclohexyl)ethylpropanedioic acid ethyl ester, diphenyl oxide, 4-(methylethyl)cyclohexan-1-ol, and 2-methylpropanoic acid 2-phenoxyethyl ester; wherein the formula described herein further comprises 5% to 60% of two or more additional compounds selected from the group consisting of: 2-phenoxyethanol (CAS #122-99-6), ethyl 10-undecenoate (CAS #692-86-4), 2-methylundecanal (also Aldehyde C-12; MNA) (CAS #110-41-8), Cyclacet® (3a,4,5,6,7,7a-hexahydro-4,7-methano-1h-inden-5(or 6)-yl acetate) (CAS #54830-99-8), and hexyl salicylate (CAS #6259-76-3).

In one or more embodiments, the present invention provides for a Malodor Counteractant (MOC) formula comprising 1-(3-3 dimethylcyclohexyl)ethylpropanedioic acid ethyl ester, diphenyl oxide, 4-(methylethyl)cyclohexan-1-ol, and 2-methylpropanoic acid 2-phenoxyethyl ester; wherein the formula described herein further comprises 10% to 50% of one or more additional compounds selected from the group consisting of: 2-phenoxyethanol (CAS #122-99-6), ethyl 10-undecenoate (CAS #692-86-4), and 2-methylundecanal (also Aldehyde C-12; MNA) (CAS #110-41-8).

In one or more embodiments, the present invention provides for a Malodor Counteractant (MOC) formula comprising 1-(3-3 dimethylcyclohexyl)ethylpropanedioic acid ethyl ester, diphenyl oxide, 4-(methylethyl)cyclohexan-1-ol, and 2-methylpropanoic acid 2-phenoxyethyl ester; wherein the formula described herein further comprises 10% to 30% of one or more additional compounds selected from the group consisting of: 2-phenoxyethanol (CAS #122-99-6), 2-methylundecanal (also Aldehyde C-12; MNA) (CAS #110-41-8), Cyclacet® (3a,4,5,6,7,7a-hexahydro-4,7-methano-1h-inden-5(or 6)-yl acetate) (CAS #54830-99-8).

In one or more embodiments, the present invention provides for a Malodor Counteractant (MOC) formula comprising 1-(3-3 dimethylcyclohexyl)ethylpropanedioic acid ethyl ester, diphenyl oxide, 4-(methylethyl)cyclohexan-1-ol, and 2-methylpropanoic acid 2-phenoxyethyl ester; wherein the formula described herein further comprises 10% to 30% of one or more additional compounds selected from the group consisting of: 2-phenoxyethanol (CAS #122-99-6), ethyl 10-undecenoate (CAS #692-86-4), 2-methylundecanal (also Aldehyde C-12; MNA) (CAS #110-41-8), and hexyl salicylate (CAS #6259-76-3).

In one or more embodiments, the present invention provides for a Malodor Counteractant (MOC) formula comprising 1-(3-3 dimethylcyclohexyl)ethylpropanedioic acid ethyl ester, diphenyl oxide, 4-(methylethyl)cyclohexan-1-ol, and 2-methylpropanoic acid 2-phenoxyethyl ester; wherein the formula described herein further comprises 10% to 30% of one or more additional compounds selected from the group consisting of: 2-phenoxyethanol (CAS #122-99-6), Cyclacet® (3a,4,5,6,7,7a-hexahydro-4,7-methano-1h-inden-5(or 6)-yl acetate) (CAS #54830-99-8), and hexyl salicylate (CAS #6259-76-3).

In one aspect, the malodor reduction composition's mixture is present in a final composition in an amount up to 100%, by weight of the malodor reduction composition, alternatively from about 5% to about 100%, alternatively from about 10% to about 100%, alternatively from about 30% to about 100%, alternatively from about 50% to about 100%, alternatively from about 70% to about 100%, alternatively from about 80% to about 100%, alternatively from about 0.01% to about 95%, alternatively from about 0.01% to about 85%, alternatively from about 0.01% to about 75%, alternatively from about 0.01% to about 65%, alternatively from about 0.01% to about 55%, alternatively from about 0.01% to about 45%, alternatively from about 0.01% to about 35%, alternatively from about 0.01% to about 25%, alternatively from about 0.1% to about 15%, alternatively from about 0.001% to about 10%, alternatively from about 0.001% to about 5%, alternatively from about 0.001% to about 5%, alternatively from about 0.001% to about 3%, alternatively from about 0.001% to about 1%, alternatively about 0.001% to about 0.5%, by weight of the malodor reduction composition.

In one or more embodiments, the present invention provides for a Malodor Counteractant (MOC) formula consisting of (i) 1-(3-3 dimethylcyclohexyl)ethylpropanedioic acid ethyl ester, (ii) diphenyl oxide, and (iii) 4-(methylethyl)cyclohexan-1-ol ranging from 2% to 40% each and (iv) 2-methylpropanoic acid 2-phenoxyethyl ester ranging from 20% to 60% each neutralized urine odors, sweat odors, and pet odors. The ingredients work synergistically as a compound and not as well individually.

In certain embodiments, the Malodor Counteractant (MOC) formula is used at 100% of the IFRA recommended level for that consumer product category. Alternatively, from 1% to about 99/% of a perfume formula is utilized. The MOC is effective at from 1, 2, 3, 4, 5 ppm or more in detergents and 100 ppm to 100% of the IFRA recommended level for other consumer product category.

Many known conventional odor counteractants, such as zinc ricinoleate, also react with fragrances. Therefore, a fragrance containing a conventional odor counteractant changes strength and character of the fragrance and has continual reduction of the efficacy of the odor counteractant and the bloom of the fragrance. The malodor counteractant compounds of the present invention provide for a unique composition that does not react with the fragrance yet still blocks odors.

In one or more embodiments, the Malodor Counteractant (MOC) formula can be used in fragrance formulas at a concentration of from about 10 ppm to about 2000 ppm. In additional embodiments, the Malodor Counteractant (MOC) formula can be used in fragrance formulas at a concentration of from about 50 ppm to about 1000 ppm. In one or more other embodiments, the Malodor Counteractant (MOC) formula can be used in fragrance formulas at a concentration of from about 100 ppm to about 500 ppm.

In one or more embodiments, the Malodor Counteractant (MOC) formula can be used as part of a fragrance formula or added to personal care products from 0.1% up to 20% based on weight percent. For diapers, catamenials, dog pee-pads, panty shields, and other absorbent pads it is effective from 50 ppm up to 2.5% maximum per International Fragrance Research Association (IFRA) guidelines.

In one or more embodiments, the malodor control composition can be formulated in with other raw materials in an amount, for example, of about 10% by weight of the Malodor Counteractant (MOC) formula.

In the present invention, it has been discovered that the MOC formula, when compounded four times eliminating one ingredient and replacing it with odorless dipropylene glycol (diluent), the resulting compounds failed to provide the synergistic effect shown by the combination formula. When the resulting compounds were re-evaluated, the performance of the MOC compound (when missing at least one ingredient) was found less effective, proving each ingredient was vital to the synergistic odor-controlling effect. Analysis by gas chromatography columns shows the elution times of these components in this compound match the elution times of the urine malodor, the isovaleric acid, propionic acid and hexanoic acid.

Embodiments of this invention include compositions and methods for reducing or eliminating odors emitted by substrate. Substrates that can be treated by embodiments of this invention include smoke, sweat, fecal matter, vomit, urine, or sewage sludge, which can create environmental malodors.

The present invention provides for odor eliminating compositions. In one or more embodiments, the compositions are aqueous based and include: (a) Malodor Counteractant (MOC) formula; (b) at least one odor neutralizing agent; and (c) at least one dispersant.

In an additional one or more embodiments, the composition further comprises one or more of the following: (d) at least one fragrance; (e) at least one buffering system; and (f) at least one surfactant.

In one or more embodiments, the at least one odor neutralizing agent is selected from the group consisting of chlorinated oxidizers (e.g., chlorine dioxide), aldehydes, permanganates, peroxides, metal oxides, borates, borax, perborates, enzymes, urease inhibitors, proteases, cationic surfactants (e.g., N-ethyl-N-soyamorpholiniumethosulphate), metallic salts (e.g., zinc salts, zinc ricinoleate, zinc chloride, zinc gluconate), metal ions (e.g., transition metal ions), nano-particulate metal ions (e.g., ferric and aluminum salts), silver, copper, zinc, carbon (e.g., activated), oxides, cyclodextrins, zeolites, activated carbon, activated alumina, calcium carbonate, silicas, clay minerals, chlorophyll, metal organic frameworks ("MOFs"), molecular sieves, and chelating agents and metal binders such as EDTA or any combinations thereof.

In one or more embodiments, the at least one odor neutralizing agent comprises from about 0.05% to 5.0% (wt) or 500 ppm to 50,000 ppm of the final product. In one or more embodiments, the at least one odor neutralizing agent comprises from about 0.005% to 0.5% (wt) or 50 ppm to 5,000 ppm of the final product.

In one embodiment, the at least one odor neutralizing agent is selected from the group consisting of zeolites, activated carbons, zinc salts, zinc oxides, cyclodextrins, fatty alcohol esters, aliphatic aldehydes (C10, C11, and C12), zinc ricinoleate actives, benzaldehyde, soyethyl morpholinium ethosulfate, Meelium®, and Metazene®.

Exemplary neutralizing agents include substituted esters such as lauryl methacrylate, sold under the trade name Metazene® and disclosed in, for example, U.S. Pat. Nos. 2,554,093, 4,009,254, 4,257,176 as well as others, biguanides and quaternary ammonium compounds, such as those disclosed in U.S. Pat. No. 4,818,524; and esters of unsaturated monocarboxylic acids, such as those disclosed in U.S. Pat. No. 3,074,981, the contents of each of which are expressly incorporated by reference herein in their entireties.

In one embodiment, the at least one odor neutralizing agent is an organic zinc salt. "Organic zinc salts" refers to zinc salts of organic carboxylic acids having 2 to 30 carbon atoms, in particular 12 to 24 carbon atoms are preferably used. The carboxylic acid group may be attached to aliphatic, aliphatic-aromatic, aromatic aliphatic, alicyclic or aromatic residues, wherein the aliphatic chain or the alicyclic ring(s) may be unsaturated and are optionally substituted for instance by hydroxyl or C1 to C4 alkyl. These salts include zinc acetate, zinc lactate, zinc ricinoleate and zinc abietate. More preferably, the zinc salt is the zinc salt of an unsaturated hydroxylated fatty acid having 8 to 18 carbon atoms. Although there is no specific restriction regarding the number of unsaturated double bonds or hydroxy groups, those fatty acids having one or two unsaturated double bonds and one or two hydroxyl groups seem to be preferred. The most preferred embodiment is zinc ricinoleate. Zinc ricinoleate is the zinc salt of ricinoleic acid, a major fatty acid found in castor oil. It is used in many deodorants as an odor-neutralizing agent.

Zinc salts and zinc ricinoleate were found to react with the fragrance and change the character of the odor.

One or more embodiments may include laundry detergents, additive, and the like for leave-on, through the wash, and rinse-off type of applications.

The malodor control composition may, optionally, include odor masking agents, odor blocking agents, and/or diluents. Odor-masking may include a compound with a non-offensive or pleasant smell that is dosed such it limits the ability to sense a malodorous compound. Odor-masking may involve the selection of compounds, which coordinate with an anticipated malodor to change the perception of the overall scent provided by the combination of odorous compounds. As used herein, the term "masking agent" refers to a perfume or fragrant compound that imparts a scent to mask the malodor. Common fragrances are within this category.

The malodor control composition may also, optionally, include perfume raw materials that solely provide a hedonic benefit (i.e. that do not neutralize malodors yet provide a pleasant fragrance).

An absorbent article comprising a malodor control composition and methods of use thereof, is also provided.

The absorbent article can comprise sanitary napkins. The absorbent articles herein are preferably disposable after a single use.

The malodor control composition of the present invention can be deposited in various locations in the absorbent article. The malodor control composition can be disposed on the garment-facing side or the body-facing side of the topsheet or absorbent core, or the body-facing side of the backsheet. Preferably, the malodor control composition is disposed on the absorbent core, and preferably on the garment-facing side of the absorbent core. The malodor control composition can also be deposited on other components, when present in the absorbent article, such as the garment-facing side or body-facing side of a secondary topsheet or acquisition layer.

In one or more embodiments, the present invention provides for Malodor Counteractant (MOC) formulas above, which further comprise one or more of the following additional ingredients: Adoxal N.P., Alcohol C-10, Aldehyde C-10, Aldehyde C-11 Lenic, Aldehyde C-11 MOA, Aldehyde C-12 Lauric, Allyl Amyl Glycolat, Allyl Cyclohexyl Proprionate, Amyl Acetate, Anisic Aldehyde, Benzyl Acetate, Benzyl Salicylate, Bergamot Oil, Cis-3-Hexenyl Acetate, Cis-3-Hexenyl Salicylate Extra, Citronellol 850/950, Cyclamen Aldehyde Extra, Cyclaprop, Dihydro Myrcenol, DimethylBenzyl Carbinyl Acetate, Dimethyl Benzyl Carbinyl Butyrate, Dimethyl Octanol, Dimetol, EthylButyrate, Ethyl Linalool, Ethylene Brassylate, Eucalyptol Oil 80% Nat., Evernyl, Florate, Floralozone, Floropal/Corps 717, Florosa, Geranyl Acetate Extra, Heliotropine, Hexyl Acetate, Hexyl Cinnamic Aldehyde, Hexyl Salicylate, Ionone Alpha Regular, Ionone Beta, Iso E Super, Jasmal, Lavandin ABS, Lavandin Oil Abrialis, Lemon Terpenes, Linalool, Linalyl Acetate, Melonal, Methyl Dihydro Jasmonate, Musk 144-D, Myrac Aldehyde, Nerolin Bromelia, Orange Terpenes, Ozonil, Pentadecanolide, Phenoxanol, Phenoxy-2-Ethanol, Precyclomone B, PrenylAcetate, Sandalore, Tetrahydro Muguol, Trans Decanal, Undecavertol, Vandor B, Verdox, Vertocitral C, and Zestoril.

A composition according to any preceding embodiment, the malodor reduction composition being a consumer product, the consumer comprising a total of, based on total consumer product weight, from about 0.0001% to about 100% of one or more of the malodor reduction materials and an adjunct material is disclosed.

The malodor counteractant compounds of the invention can be used in a variety of forms and in a variety of products. Thus, in certain embodiments, the present invention features a method for counteracting a malodor by introducing or adding one or more malodor counteractant compounds to an air space (e.g., the surrounding environment) or a substrate so that the malodor of the product is counteracted. The malodor counteractant compounds can be used alone or provided in the form of a consumer, industrial, textile, flavor or food product. As such, the compounds, products, and methods of the invention can be pursued in any situation where malodor is present.

For the purposes of the present invention, a compound counteracts a malodor if it measurably (either qualitatively or quantitatively) reduces the perception or intensity of a malodor. In particular embodiments, a malodor counteractant compound of the present invention reduces the perception or intensity of an isolated malodor by 50-100% as compared to the malodor in the absence of the malodor counteractant compound. When the malodor counteractant compound is used in combination with a fragrance, the fragrance can result in a further reduction in the perception or intensity of a malodor. In particular embodiments, a malodor counteractant compound of the invention reduces the perception or intensity of a malodor by at least 50, 55, 60, 65, 70, 75, 80, 85, 90, 95, 97, 98, 99 or 100% as compared to the malodor in the absence of the malodor counteractant compound.

Malodors particularly targeted by the compounds of the invention include malodors such as bathroom odors, sweat, food odors, textile odors, home care and personal care product base odors, adhesive odors, and paint odors. Thus, the compounds of the invention can be used in products including, but not limited to, air refresheners, fabric refresheners, bar soaps, perfumes, fragrances, cologne, bath or shower gels, shampoos or other hair care products, cosmetic preparations, body odorants, deodorants, antiperspirants, liquid or solid fabric detergents or softeners, bleach products, disinfectants or all-purpose household or industrial cleaners, food, or industrial or textile products such as adhesives, paints, coatings, or textiles.

The composition of the invention can be in the form of an aerosol or other spray, fragrance diffusers, a wick or other liquid system, or a solid, for instance candles or a wax base as in pomanders and plastics, powders as in sachets or dry sprays or gels, as in solid gel sticks, clothes deodorants as applied by washing machine applications such as in detergents, powders, liquids, whiteners or fabric softeners, fabric refreshers, linen sprays, closet blocks, closet aerosol sprays, or clothes storage areas or in dry cleaning to overcome residual solvent notes on clothes, bathroom accessories such as paper towels, bathroom tissues, sanitary napkins, towelettes, disposable wash cloths, disposable diapers, and diaper pail deodorants, cleansers such as disinfectants and toilet bowl cleaners, cosmetic products such as antiperspirant and deodorants, general body deodorants in the form of powders, aerosols, liquids or solid, or hair care products such as hair sprays, conditioners, rinses, hair colors and dyes, permanent waves, depilatories, hair straighteners, hair groom applications such as pomade, creams and lotions, medicated hair care products containing such ingredients as selenium sulfide, coal tar or salicylates, or shampoos, or foot care products such as foot powders, liquids or colognes, after shaves and body lotions, or soaps and synthetic detergents such as bars, liquids, foams or powders, odor control such as during manufacturing processes, such as in the textile finishing industry and the printing industry (inks and paper), effluent control such as in processes involved in pulping, stock yard and meat processing, sewage treatment, garbage bags, or garbage disposal, or in product odor control as in textile finished goods, rubber finished goods or car fresheners, agricultural and pet care products such as dog and hen house effluents and domestic animal and pet care products such as deodorants, shampoo or cleaning agents, or animal litter material and in large scale closed air systems such as auditoria, subways and transport systems, and in food applications such as gum, hard candy, confectionery, food packaging, etc. In addition, the malodor counteractant compound can be used in a fine fragrance composed of the malodor counteractant compound and a fragrance.

In one or more embodiments, the consumer product is a room freshener spray, a fragrance diffuser, a candle, a sachet, a clothes deodorant, a detergent, a fabric softener, a fabric refresher, a linen spray, a disposable diaper, a diaper pail deodorant, an antiperspirant, a deodorant, a garbage bag, a car freshener, a pet care product, an animal litter material or a fine fragrance.

The composition of the invention is usually one in which the malodor counteractant compound is present together with a carrier by means of which, or from which, the malodor counteractant compound can be introduced into air space wherein the malodor is present, or a substrate on which the malodor has been deposited. For example, the carrier can be an aerosol propellant such as a chlorofluoromethane or isobutane, or a solid such as a wax, plastics material, rubber, inert powder or gel. In a wick-type air freshener, the carrier is a substantially odorless liquid of high volatility. In several applications, a composition of the invention contains a surface-active agent or a disinfectant, while in others, the malodor counteractant compound is present on a fibrous substrate. In still other embodiments, a composition of the invention also includes a fragrance selected from those described herein.

In one aspect, the malodor reduction composition that is a consumer product is air care composition that comprises a total of, based on total consumer product weight, from about 0.001% to about 100%, in one aspect, from 0.01 to 10%, of one or more of the malodor reduction materials and, optionally, one or more materials selected from the group consisting of surfactants, antimicrobial agents, wetting agents, buffering agents, cyclodextrins, propellants, and solvents.

In one aspect, the malodor reduction composition that is a consumer product is an absorbent litter composition that comprises a total of, based on total consumer product weight, from about 0.001% to about 100%, in one aspect, from 0.01 to 10%, of one or more of the malodor reduction materials and, optionally, one or more materials selected from the group consisting of surfactants, antimicrobial agents, wetting agents, buffering agents, cyclodextrins, propellants, and solvents. The term "litter(s)" means a composition that is suitable for use as an animal litter (e.g., managing animal waste) but that can also be used for any other suitable purpose. For example, a litter described herein could be used to absorb a chemical spill, absorb an oil spill, create traction on a slippery surface, and the like.

The present invention provides for composite absorbent particles with improved physical and chemical properties comprising an absorbent material and optional performance-enhancing actives.

A preferred use for the absorbent particles is as a cat litter, and therefore much of the discussion herein will refer to cat litter applications. However, it should be kept in mind that the absorbent particles have a multitude of applications, and should not be limited to the context of a cat litter.

Many liquid-absorbing materials may be used without departing from the spirit and scope of the present invention. Illustrative absorbent materials include but are not limited to minerals, fly ash, absorbing pelletized materials, perlite, silicas, recycled paper, pine bark, pelletized corn cobs or other absorbent materials and mixtures thereof. Preferred minerals include: bentonites, zeolites, fullers earth, attapulgite, montmorillonite diatomaceous earth, opaline silica, Georgia White clay, sepiolite, calcite, dolomite, slate, pumice, tobermite, marls, attapulgite, kaolinite, halloysite, smectite, vermiculite, hectorite, Fuller's earth, fossilized plant materials, expanded perlites, gypsum and other similar minerals and mixtures thereof. The preferred absorbent material is sodium bentonite having a mean particle diameter of about 5000 microns or less, preferably about 3000 microns or less, and ideally in the range of about 25 to about 150 microns.

Calcium bentonite may be added to reduce sticking to a litter box. The litter may also include a binder such as water, lignin sulfonate (solid), polymeric binders, fibrillated Teflon (polytetrafluoroethylene or PTFE), and combinations thereof. Useful organic polymerizable binders include, but are not limited to, carboxymethylcellulose (CMC) and its derivatives and its metal salts, guar gum cellulose, xanthan gum, starch, lignin, polyvinyl alcohol, polyacrylic acid, styrene butadiene resins (SBR), and polystyrene acrylic acid resins. Water stable particles can also be made with crosslinked polyester network, including but not limited to those resulting from the reactions of polyacrylic acid or citric acid with different polyols such as glycerin, polyvinyl alcohol, lignin, and hydroxyethylcellulose.

In one aspect, the malodor reduction composition that is a consumer product is a plastic film the plastic film comprising LLDPE, LDPE, HDPE, and/or compostable film, in one aspect, the plastic film comprises about 0.5 mg to about 100 mg of the malodor reduction composition per 20 grams of the plastic film, in one aspect, the malodor reduction composition is present in the amount of about 5 mg to about 30 mg per 20 grams of the plastic film, in one aspect, the malodor reduction composition is present in the amount of about 5 mg to about 15 mg per 20 grams of the plastic film.

In one aspect, the malodor reduction composition that is a consumer product is an absorbent article the absorbent article comprising a total of, based on total consumer product weight, from about 100 ppm to the IFRA limit of 2.5% of one or more of the malodor reduction materials and, wherein the article comprises a topsheet, a backsheet, an absorbent core disposed between the topsheet and the backsheet, and an acquisition layer disposed between the topsheet and the absorbent core, wherein the malodor reduction composition is disposed on one of the backsheet, absorbent core, or acquisition layer, in one aspect, the absorbent article comprises a hot melt adhesive and the hot melt adhesive comprises the malodor reduction composition, in one aspect, the hot melt adhesive adheres the backsheet to the topsheet, in one aspect, the backsheet comprises a nonwoven layer and a film layer, and the hot melt adhesive adheres the backsheet nonwoven layer to the backsheet film layer.

In one aspect, the malodor reduction composition that is a consumer product is a personal care deodorant composition, the deodorant composition comprising a total of, based on total consumer product weight, from about 0.1% to about 5% of one or more of the malodor reduction materials and, optionally, from about 0.01% to about 75% of an antimicrobial, in one aspect, the antimicrobials are selected from the group consisting of metals, zeolites, metal zeolites, quaternary ammonium (quat) compounds (e.g., cetyl pyridinium chloride, and benzylalkonium chloride), quat bound clays, metal bound clays, polyaspirin. salicylic acid, polyvinyl amines, coal tar, sulfur, whitfield's ointment, castellani's paint, aluminum chloride, gentian violet, octopirox (piroctone olamine), ciclopirox olamine, undecylenic acid and it's metal salts, potassium permanganate, selenium sulfide, sodium thiosulfate, glycols, diols, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, citronellic acid, hinokitol, ichthyol pale, Sensiva SC-50, Elestab HP-100, azelaic acid, lyticase, iodopropynyl butylcarbamate (IPBC), triclosan, triclocarban, isothiazalinones and azoles, and combinations thereof, more preferably, hexanediol, triclosan, octyl isothiazalinone metals selected from the group consisting of Zn, Cu, Al, Ti, Sn, Bi, and Ag, metal salts selected from the group consisting of zinc carbonate, copper sulfate, and zinc gluconate, metal pyrithione salts selected from the group consisting of ZPT and CuPT, glycols selected from the group consisting of propylene glycol, dipropylene glycol and hexylene glycol and mixtures thereof, in one aspect, the personal care deodorant composition comprises, based on total deodorant weight, from about 100 ppm to about 20% IFRA limit.

In one aspect, the malodor reduction composition that is a consumer product is a personal care body wash/shampoo composition, the body wash/shampoo comprising a total of, based on total consumer product weight, from about 0.1% to about 7% of one or more of the malodor reduction materials from about 3% to 30% of a surfactant, and, optionally, a miscellar phase and/or lamellar phase.

In one aspect, the malodor reduction composition that is a consumer product is a personal care antiperspirant composition. The product may be a stick, roll-on, aerosol or cream/gel and contain antiperspirant actives comprising a total of from about 1% to about 25% of an antiperspirant actives selected from the group consisting of astringent metallic salts, in one aspect, inorganic and organic salts of aluminum, zirconium and zinc, as well as mixtures thereof, in one aspect, aluminum halides, aluminum chlorohydrate, aluminum hydroxyhalides, zirconyl oxyhalides, zirconyl hydroxyhalides, and aluminum chloride hexahydrate, zirconium chloride, as well as aluminum zirconium tetrachlorohydrate mixtures thereof. And the Malodor Control compound cited in this patent from about 100 ppm to 2% of one or more of the malodor reduction materials, and a fragrance for consumer appeal.

In one aspect, the malodor reduction composition that is a consumer product personal deodorant composition in an aerosol, gel, stick or roll-on comprising a total of a non active base with an antimicrobial to control odor generating bacteria, and from about 100 ppm to 5% of the Malodor Control compound cited in this patent and a fragrance for consumer appeal.

In one aspect, the malodor reduction composition that is a consumer product is a dish cleaning composition, the dish cleaning composition comprising a total of, based on total consumer product weight, from about 100 ppm to 5% of one or more of the malodor control compound cited in this patent and a fragrance for consumer appeal.

In one aspect, a method of controlling malodors comprising: contacting the material comprising a malodor with a composition selected from the group consisting of any of the compositions comprising a malodor reduction material disclosed herein and mixtures thereof, in one aspect, the contacting step comprises contacting the material containing a malodor with about 1 mg to about 50 mg, from about 3 mg to 30 mg, or from about 5 mg to about 20 mg of the composition per 20 grams of the material containing a malodor is disclosed.

In one aspect, a method of controlling urine malodor on nursing home sheets which detergents do not remove after repeated washings. The malodor reduction composition herein can be administered in a detergent or a fabric softener at 5 to 100 ppm in the final wash concentration.

In one aspect, a method of determining the material's ability to decrease or even eliminate the perception of one or more malodors is disclosed.

Perfume Mixture

The malodor control composition may include a mixture of perfume raw materials such as volatile aldehydes, esters and/or alcohols. One or more of the perfume materials may comprise an activated alkene.

The malodor control composition may include perfume raw materials that provide a functional (e.g. malodor removal, assisting with volatilization of compounds) and/or a hedonic benefit (i.e. primarily present to provide a pleasant fragrance). Suitable perfumes are disclosed in U.S. Pat. No. 6,248,135, which is incorporated in its entirety by reference.

In other embodiments, the malodor control composition contains no perfume raw materials. While there may be some scent from certain constituents of the malodor control composition, because of its low odor threshold it may be used for it's odor blocking abilities in a fragrance free product. In Fragrance free consumer products, the compositions can be listed as fragrance free because the compositions are being used to control odors not scent the material.

In one or more embodiments, the perfume mixture can be formulated into the malodor control composition in any desired amount, for example, at about 1%, alternatively from about 0.01% to about 10%, alternatively from about 0.05% to about 5%, alternatively from about 0.5% to about 2%, by weight of the malodor control composition.

In some embodiments where volatility is not important for neutralizing a malodor, the present invention may include poly-aldehydes, for example, di-, tri-, tetra-aldehydes. Such embodiments may include laundry detergents, additive, and the like for leave-on, through the wash, and rinse-off type of applications.

In one or more embodiments, the dispersed phase may comprise a perfume that may include materials selected from the group consisting of perfumes such as 3-(4-t-butylphenyl)-2-methyl propanal, 3-(4-t-butylphenyl)-propanal, 3-(4-isopropylphenyl)-2-methylpropanal, 3-(3,4-methylenedioxyphenyl)-2-methylpropanal, and 2,6-dimethyl-5-heptenal, alpha-damascone, beta-damascone, delta-damascone, beta-damascenone, 6,7-dihydro-1,1,2,3,3-pentamethyl-4(5H)-indanone, methyl-7,3-dihydro-2H-1,5-benzodioxepine-3-one, 2-[2-(4-methyl-3-cyclohexenyl-1-yl)propyl]cyclopentan-2-one, 2-sec-butylcyclohexanone, and beta-dihydro ionone, linalool, ethyllinalool, tetrahydrolinalool, and dihydromyrcenol.

Surfactants

Compositions of the present invention can optionally include one or more surfactants to promote compatibility of the compositions and to help wet the surface and/or to aid in contacting and controlling or killing microorganisms or preventing toxin production. As used herein the term "surfactant" means an amphiphile (a molecule possessing both polar and nonpolar regions which are covalently bound) capable of reducing the surface tension of water and/or the interfacial tension between water and an immiscible liquid. The term is meant to include soaps, detergents, emulsifiers, surface active agents, and the like. The surfactant can be cationic, anionic, nonionic, or amphoteric. A variety of conventional surfactants may be used; however, it may be important in selecting a surfactant to determine that it is compatible with the finished compositions and does not inhibit the antimicrobial activity of the antimicrobial composition. One skilled in the art can determine compatibility of a surfactant by making the formulation and testing for antimicrobial activity as described in the Examples herein. Combinations of various surfactants can be used. Preferred surfactants are selected from the surfactants based on sulfates, sulfonates, phosphonates, phosphates, poloxamers, alkyl lactates, carboxylates, cationic surfactants, and combinations thereof and more preferably is selected from (C8-C22) alkyl sulfate salts, di(C8-C18)sulfosuccinate salts, C8-C22 alkyl sarconsinate, and combinations thereof.

Non-limiting examples of suitable surfactants include ethoxylated hydrogenated castor oils, ethoxylated alcohols, and polyalkylene oxide polysiloxanes, and combinations thereof.

The surfactant is typically present at a level of from about 0.1% to about 60%, from about 1% to about 50%, from about 2% to about 40%, from about 3% to about 30%, from about 5% to about 20%, by weight of the subject composition.

The surfactant is present in an effective amount to achieve dispersion or emulsification of the activated alkenes, perfume raw materials, or other materials in the malodor control composition.

In one embodiment, these effective amounts of surfactant may be, for example, less than about 3%, alternatively from about 0.01% to about 1%, alternatively from about 0.05% to about 0.5%, by weight of the composition.

One or more surfactants may be used at a suitable level to produce the desired result. In some embodiments, when used in the composition, they are present in a total amount of between about 0.1 wt. % to about 5 wt-%, based on the total weight of the antimicrobial composition.

In one embodiment, the at least one surfactant is included in an amount of about 0.1 to about 10 wt. % of the composition, preferably about 0.1 to about 5 wt. %. The surfactant serves as a solubilizer alone or in conjunction with the alkylene glycol component for the fragrance, preservative or other component, which may be present that is not soluble in the aqueous carrier of the composition. Surfactants otherwise suitable for use can be nonionic, anionic, amphoteric, cationic, or a combination thereof.

Nonionic surfactants suitable for use in the compositions of the present invention include alkoxylated compounds such as, for example, fatty alcohol alkoxylates, alkoxylated polyol fatty acid esters; alkyl polyglucosides; alkanolamides, including fatty acid alkanolamides; fatty alcohol polyalkyleneglycol ethers; oxo-alcohol polyalkylene glycol ethers; alkylphenol polyalkylene glycol ethers; fatty alcohol poly-poly glycol ethers (e.g. ethylene oxide/propylene oxide adducts); and alkyl dimethyl amine oxide, as well as non-ionic polymers such as for example ethylene oxide/propylene oxide block copolymers. The alkoxy component is preferably ethoxy.

Anionic surfactants suitable for use in the compositions of the present invention include soaps, alkyl benzene sulfonates, alkane sulfonates, alpha-olefin sulfonates; alpha-sulfo fatty acid methyl esters; fatty alcohol sulfates or alkyl sulfates; alkyl ether sulfates including fatty alcohol ether sulfates and oxo-alcohol ether sulfates; and the like, as well as combinations thereof.

Examples of the quaternaries include oleyl di(polyoxyethylene)methyl ammonium chloride, stearyl dimethyl benzyl ammonium chloride, distearyldimethylanunonium chloride, stearyl trimethyl ammonium chloride, stearyl tri (polyoxyethylene)ammonium chloride, polyoxypropylene methyl diethyl ammonium chloride, myristyl dimethyl benzyl ammonium chloride, lauryl trimethyl ammonium chloride, etc.

Examples of the amphoteric surfactant include 2-alkyl-N-carboxymethyl-N-hydroxyethyl imidazolinium betaine, sodium undecyl hydroxyethyl imidazolinium betaine, undecyl-N-hydroxyethyl-N-carboxymethyl imidazolinium betaine, stearyl dihydroxyethyl betaine, coconut oil fatty acid amidopropyl betaine, sodium coconut oil alkyl-N-carboxyethyl-N-hydroxyethyl imidazolinium betaine, disodium coconut oil alkyl-N-carboxymethoxyethyl-N-carboxymethyl imidazolinium lauryl sulfate, N-coconut oil fatty acid acyl-L-arginine ethyl-DL-pyrrolidone-carboxylate, etc.

In additional to surfactants, the diluted water-soluble concentrate of the present invention may be used with conventional solvents, dyes, preservatives, emulsifying agents, perfumes, antibacterial agents, thickeners, conditioners, antistatic agents, silicone surfactants, and other like ingredients that are typically present in conventional home care formulations. Mixtures and/or combinations of the aforementioned additional formulating agents may also be employed in the present invention. The amounts of the additional formulating agents that may be employed in the present invention are within ranges that are well known to those skilled in the art and further formulating is performed using processes that are also well known in the art.

Dispersants

The compositions of the present invention can also contain dispersants. Suitable water-soluble organic materials include the homo- or co-polymeric acids or their salts, in which the polycarboxylic acid comprises at least two carboxyl radicals separated from each other by not more than two carbon atoms.

A dispersant can be important to suspend the microcapsules in the composition to prevent the microcapsules from falling out of solution. Thus a dispersant can be important in achieving a composition that is stable.

When the present compositions are designed to be sprayed from a spray dispenser, it can be important to select a level and type of dispersant that provides enough suspension for microcapsule particles, but at the same time is easily sprayable as a fine mist. Some dispersants are capable of suspending particles, but result in compositions having viscosities that are too high to be easily sprayable as a fine mist.

In this respect, the level and type of dispersant is preferably selected to provide a non-Newtonian viscosity property. The resulting malodor-controlling compositions are capable of adequately suspending particles therein (e.g. microcapsules) while being easily sprayable from a spray dispenser.

The preferred dispersants herein provide a shear-thinning composition having a weak gel formation matrix, in which polymeric or non-polymeric ingredients interact with each other and form hydrogen and/or hydrophobic bonding. Some functional groups on the molecules have electrostatic repulsive forces that can prevent coagulation of the particles in the composition. The weakly formed gel matrix resulting from the preferred dispersants herein is capable of suspending micron size particles, such as microcapsules, in the composition matrix.

When present, dispersants are typically included at a level of from about 0.001% to about 10%, preferably from about 0.005% to about 5%, and more preferably from about 0.01% to about 1%, by weight of the composition. If it is desired to keep the viscosity of the present compositions relatively low, e.g. if the compositions are to be sprayed onto surfaces (e.g. fabrics) via a spray dispenser, the dispersant is preferably included at a level of less than about 1%, more preferably less than about 0.9%, and even more preferably less than about 0.8%, by weight of the composition. If the level of dispersant is too high, the composition may leave a visible residue on the treated surfaces. If the composition is to be sprayed on fabrics and the level of dispersant is too high, the composition may undesirable alter the fabric feel or softness.

The dispersants herein can be selected from materials such as pectine, alginate, arabinogalactan, carageenan, gellan gum, xanthum gum, guar gum, acrylates/acrylic polymers, water-swellable clays, fumed silicas, acrylate/aminoacrylate copolymers, and mixtures thereof. Preferred dispersants herein include those selected from the group consisting of acrylate/acrylic polymers, gellan gum, fumed silicas, acrylate/aminoacrylate copolymers, water-swellable clays, and mixtures thereof.

Carriers

The composition of the invention is usually one in which the malodor counteractant is present together with a carrier by means of which or from which the malodor counteractant can be introduced into air space wherein the malodor is present, or a substrate on which the malodor has deposited. For example, the carrier can be an aerosol propellant such as a chlorofluoro-methane, or a solid such as a wax, plastics material, rubber, inert powder or gel. In a wick-type air freshener, the carrier is a substantially odorless liquid of low volatility. In several applications, a composition of the invention contains a surface-active agent or a disinfectant, while in others, the malodor counteractant is present on a fibrous substrate. In many compositions of the invention there is also present a fragrance component, which imparts a fragrance to the composition. The fragrances stated above can all be employed.

Exemplary diluents include dipropylene glycol methyl ether, and 3-methoxy-3-methyl-1-butanol, apricot kernel oil and other natural oils and mixtures thereof.

Aqueous Carrier

The malodor control composition, with a suitable solubilizer, of the present invention may include an aqueous carrier. The aqueous carrier may be distilled, deionized, or tap water. The level of aqueous carrier in the present compositions can vary dependent upon the use of the composition. In general, the level of aqueous carrier in the present compositions can be from about 0.1% to about 99.9%. In compositions designed to be sprayed from manually or non-manually operated spray dispensers, the level of aqueous carrier is preferably high, for example, at a level of at least about 80%, preferably at least about 85%, more preferably at least about 90%, and even more preferably at least about 95%, by weight of the composition.

Water may be present in an amount of greater than 50% to about 99.5%, alternatively from about 80% to about 99.5%, alternatively from about 92% to about 99.5%, alternatively about 95%, by weight of the composition. Water containing a small amount of low molecular weight monohydric alcohols, e.g., ethanol, methanol, and isopropanol, or polyols, such as ethylene glycol and propylene glycol, can also be useful. However, the volatile low molecular weight monohydric alcohols such as ethanol and/or isopropanol should be limited since these volatile organic compounds will contribute both to flammability problems and environmental pollution problems. If small amounts of low molecular weight monohydric alcohols are present in the composition of the present invention due to the addition of alcohols to such ingredients as perfumes and as stabilizers for some preservatives, the level of monohydric alcohol may be less than about 10%, alternatively less than about 5%, alternatively less than about 1%, by weight of the composition.

Solvents

The malodor control composition may further comprise an optional one or more commercially available solvents. can help to provide compositions that dry more quickly after being applied to surfaces, versus compositions that do not contain solvent. Where it is desirable to have a composition that quickly dries after being applied to a surface, the present compositions preferably further comprise solvents. Suitable solvents herein include monohydric and polyhydric alcohols. Monohydric alcohols useful as solvents in the present composition include ethanol, n-propanol, isopropanol, mixtures thereof, and the like. Polyhydric alcohols useful as solvents in the present composition include glycols such as ethylene glycol, diethylene glycol, triethylene glycol, propylene glycol, dipropylene glycol, glycerine, mixtures thereof, and the like. Other suitable solvents include water-miscible ethers, water-miscible glycol ethers, and propylene glycol monomethyl ether acetate. Non-limiting examples of water-miscible ethers include diethylene glycol diethylether, diethyleneglycol dimethylether, propylene glycol dimethylether, and mixtures thereof. Non-limiting examples of water-miscible glycol ethers include propylene glycol monomethylether, propylene glycol monoethylether, propylene glycol monopropylether, propylene glycol monobutylether, ethylene glycol monobutylether, dipropylene glycol monomethylether, diethyleneglycol monobutylether, and mixtures thereof.

When present, the level of solvent in the present compositions is generally from about 0.1% to about 99.9%, preferably from about 0.5% to about 99%, and more preferably from about 1% to about 90%. If the compositions are spray compositions (especially non-aerosol), the level of alcohol is preferably less than about 35%, more preferably less than about 20%, and even more preferably less than about 10%, by weight of the composition.

Perfume Delivery Technologies

The compositions of the present invention may comprise one or more perfume delivery technologies that stabilize and enhance the deposition and release of perfume ingredients from treated substrate. Such perfume delivery technologies can also be used to increase the longevity of perfume release from the treated substrate. Perfume delivery technologies, methods of making certain perfume delivery technologies and the uses of such perfume delivery technologies are disclosed in US 2007/0275866 A1.

In one aspect, the compositions of the present invention may comprise from about 0.001% to about 20%, or from about 0.01% to about 10%, or from about 0.05% to about 5%, or even from about 0.1% to about 0.5% by weight of the perfume delivery technology. In one aspect, the perfume delivery technologies may be selected from the group consisting of: perfume microcapsules, pro-perfumes, polymer particles, functionalized silicones, polymer assisted delivery, molecule assisted delivery, fiber assisted delivery, amine assisted delivery, cyclodextrins, starch encapsulated accord, zeolite and inorganic carrier, and mixtures thereof.

In one aspect, the perfume delivery technology may comprise microcapsules formed by at least partially surrounding a benefit agent with a wall material. The benefit agent may include materials selected from the group consisting of perfumes such as 3-(4-t-butylphenyl)-2-methyl propanal, 3-(4-t-butylphenyl)-propanal, 3-(4-isopropylphenyl)-2-methylpropanal, 3-(3,4-methylenedioxyphenyl)-2-methylpropanal, and 2,6-dimethyl-5-heptenal, alpha-damascone, beta-damascone, delta-damascone, beta-damascenone, 6,7-dihydro-1,1,2,3,3-pentamethyl-4(5H)-indanone, methyl-7,3-dihydro-2H-1,5-benzodioxepine-3-one, 2-[2-(4-methyl-3-cyclohexenyl-1-yl)propyl]cyclopentan-2-one, 2-sec-butylcyclohexanone, and beta-dihydro ionone, linalool, ethyllinalool, tetrahydrolinalool, and dihydromyrcenol. Suitable perfume materials can be obtained from Givaudan Corp. of Mount Olive, N.J., USA, International Flavors & Fragrances Corp. of South Brunswick, N.J., USA, or Quest Corp. of Naarden, Netherlands. In one aspect, the microcapsule wall material may comprise: melamine, polyacrylamide, silicones, silica, polystyrene, polyurea, polyurethanes, polyacrylate based materials, gelatin, styrene malic anhydride, polyamides, and mixtures thereof. In one aspect, the melamine wall material may comprise melamine crosslinked with formaldehyde, melamine-dimethoxyethanol crosslinked with formaldehyde, and mixtures thereof. In one aspect, the polystyrene wall material may comprise polyestyrene cross-linked with divinylbenzene. In one aspect, the polyurea wall material may comprise urea crosslinked with formaldehyde, urea crosslinked with gluteraldehyde, and mixtures thereof. In one aspect, the polyacrylate based materials may comprise polyacrylate formed from methylmethacrylate/dimethylaminomethyl methacrylate, polyacrylate formed from amine acrylate and/or methacrylate and strong acid, polyacrylate formed from carboxylic acid acrylate and/or methacrylate monomer and strong base, polyacrylate formed from an amine acrylate and/or methacrylate monomer and a carboxylic acid acrylate and/or carboxylic acid methacrylate monomer, and mixtures thereof. In one aspect, the perfume microcapsule may be coated with a deposition aid, a cationic polymer, a non-ionic polymer, an anionic polymer, or mixtures thereof. Suitable polymers may be selected from the group consisting of: polyvinylformaldehyde, partially hydroxylated polyvinylformaldehyde, polyvinylamine, polyethyleneimine, ethoxylated polyethyleneimine, polyvinylalcohol, polyacrylates, and combinations thereof. In one aspect, the microcapsule may be a perfume microcapsule. In one aspect, one or more types of microcapsules, for example two microcapsules types having different benefit agents may be used.

Other Optional Ingredients

The malodor control composition may, optionally, include one or more radical scavengers or antioxidants, such as butylhydroxytoluene ("BHT"), ascorbic acid, alpha-tocopherol, hydroquinone ("HQ"), or hydroquinone monomethyl ether ("MeHQ"). Further, the malodor control composition may optionally contain odor-masking agents, odor blocking agents, and/or diluents. "Odor blocking" refers to the ability of a compound to combine with the malodor and create little or no detectable odor. "Odor-masking" refers to the ability of a compound to mask or hide a malodorous compound. Odor-masking may include a compound with a non-offensive or pleasant smell that is dosed such it limits the ability to sense a malodorous compound. Odor-masking may involve the selection of compounds, which coordinate with an anticipated malodor to change the perception of the overall scent provided by the combination of odorous compounds.

For example, the malodor control composition may include perfume ionones and/or a diluent in any amount. For example, a diluent may be present in an amount from about 1% to about 99.5%, alternatively from about 50% to about 99.5%, alternatively greater than 50% to about 99.5%, alternatively from about 5% to about 50%, alternatively from about 10% to about 30%, by weight of the composition. Non-limiting exemplary diluents include DBE-LVP (mixed aliphatic ester fluid (CAS #1119-40-0 and CAS #627-93-0 from INVISTA)), glycol ethers such as dipropylene glycol monomethyl ether, tripropylene glycol methyl ether, dipropylene glycol n-propyl ether, or dipropylene glycol methyl ether acetate; 3-methoxy-3-methyl-1-butanol; esters such as isononyl acetate, diethyl adipate and dioctyl adipate; benzyl alcohol; florol; Xiameter PMX-200 Silicone Fluid 1.5CS (from Dow Corning Co.); cellulose; ethyl ether; ethylene glycol; triethylene glycol; and mixtures thereof.

In one embodiment, the composition further comprises one or more of metal salts of an unsaturated hydroxy carboxylic acid. In one embodiment, the metallic salts are water-soluble zinc salts, copper salts or mixtures thereof, and more preferably zinc salts, especially zinc ricinoleate. These salts are preferably present in the present invention as an odor control agent primarily to absorb amine and sulfur-containing compounds. Low molecular weight sulfur-containing materials, e.g., sulfide and mercaptans, are components of many types of malodors, e.g., food odors (garlic, onion), body/perspiration odor, breath odor, etc. Low molecular weight amines are also components of many malodors, e.g., food odors, body odors, urine, etc.

In one embodiment, the zinc salts are selected from the group consisting of zinc borate, zinc caprylate, zinc chloride, zinc ricinoleate, zinc sulfate heptahydrate, zinc undecylenate, and mixtures thereof.

In one embodiment, the zinc salts are zinc salts of ricinoleic acid. In another embodiment, the zinc ricinoleate is combined with at least one alkoxylated amine. In another embodiment, the zinc ricinoleate is Grillocin® or Tego-Sorb®.

Zinc ricinoleate is largely insoluble in water and therefore has to be used in combination with solvents and solubility promoters in order to obtain effective preparations. The solvents used are in most cases mono- or polyhydric alcohols, optionally with the addition of water.

Grillocin® contains a clearly defined substance, zinc ricinoleate, synergistically combined with other zinc compounds made up of multiple hydroxylated sebatic acids, oxamines and resinic acids.

Tego-Sorb® is zinc ricinoleate with solubilizers and/or benzalkonium chloride. In some embodiments, the ricinoleate is in combination with one or more substituted monocyclic organic compounds.

In one embodiment, the composition is further combined with a least one further deodorizing active ingredient. In one embodiment, the at least one further deodorizing active ingredient is a quaternary ammonium compound.

In one embodiment, the at least one dispersant is selected from the group consisting of butyl ethers, Dipropylene Glycol Methyl Ether (DOWANOL), D[propylene glycol methyl ether, ethyl alcohol SDA-40, isopropyl alcohol, tropropylene, glycol (mono) methyl ether, alkylene glycol and alkyl polyglycoside.

Other agents include medium-chain triglycerides (MCTs), vegetable oils, animal oils and microalgae oils.

Medium-chain triglycerides (MCTs) are medium-chain (6 to 12 carbons) fatty acid esters of glycerol including caproic acid (C6), caprylic acid (C8), capric acid (C10) and lauric acid (C12). MCTs are composed of a glycerol backbone and three fatty acids, wherein one or more of the fatty acid chains attached to the glycerol are medium chain in length.

In one embodiment, the at least one dispersant is selected from the group consisting of butyl ethers, diethylene monethyl ether-(carbitol), D[propylene glycol methyl ether, ethyl alcohol SDA-40, isopropyl alcohol, tropropylene, glycol (mono) methyl ether, alkylene glycol, alkyl polyglycoside.

In another embodiment, the at least one dispersant is selected from the group consisting of alcohols such as methyl alcohol, ethyl alcohol, n-propyl alcohol, isopropyl alcohol; glycol ethers such as ethylene glycol monomethyl ether and triethylene glycol monoethyl ether; and any combination thereof.

Meelium is a blend of polyhydroaromatic sulfonates. Neutrolair D-7 is a mixture of geranyl crotonalte and dihexyl fumarate, Vandor B is principally 3,5,5-trimethylhexanal. Forestall is soyaethyl morpholinium ethosulfate.

Additional Odor-Reacting Compounds

Odor-reacting compounds can be used with the compositions described herein. Ammonia, amines, and thiol compounds are common odorants found in urine, vomit, and other organic contaminants. Odor-reacting compounds are those that are capable of chemically reacting with one or more of these odorants, thereby reducing or eliminating these odors. Preferably, odor-reacting compounds are selected from those compounds that do not inherently have strong odors or aromas and those that are not used as perfumes, fragrances, or aromas. Odor-reacting compounds suitable for use in the liquid or powder compositions described herein include aldehyde compounds, formaldehyde-donating compounds, ketones, and oxidizing agents.

Aldehyde compounds can react with odorous amine compounds to form an imine structure. Aldehyde compounds can also react with thiol compounds to form a thioacetal structure. Formaldehyde-donor compounds, which have similar reactivity with amines and thiols, can be used in combination or interchangeably with aldehyde compounds. The reaction of odorous amines and thiols with either the aldehyde compound or the formaldehyde-donor compound results in the products of imine and thioacetal, both of which are larger molecules than their odorous substituents. As such, these resulting structures are less volatile than their predecessors and have little to no smell.

In another embodiment, reactive aldehydes can be used as an odor control agent to mitigate the effects of malodors. Non-limiting examples of suitable reactive aldehydes include Class I aldehydes, Class H aldehydes, and mixtures thereof. Non-limiting examples of Class I aldehydes include anisic aldehyde, o-allyl-vanillin, benzaldehyde, cuminic aldehyde, ethyl-aubepin, ethyl-vanillin, heliotropin, tolyl aldehyde, and vanillin. Non-limiting examples of Class II aldehydes include 3-(4'-tert-butylphenyl)propanal, 2-methyl-3-(4'-tert-butylphenyl)propanal, 2-methyl-3-(4'-isopropylphenyl)-propanal, 2,2-dimethyl-3-(4-ethylphenyl) propanal, cinnamic aldehyde, alpha-amyl-cinnamic aldehyde, and alpha-hexyl-cinnamic aldehyde. These reactive aldehydes are described in more detail in U.S. Pat. No. 5,676,163.

Reactive aldehydes, when used, can include a combination of at least two aldehydes, with one aldehyde being selected from acyclic aliphatic aldehydes, non-terpenic aliphatic aldehydes, non-terpenic alicyclic aldehydes, terpenic aldehydes, aliphatic aldehydes substituted by an aromatic group and bifunctional aldehydes; and the second aldehyde being selected from aldehydes possessing an unsaturation alpha to the aldehyde function conjugated with an aromatic ring, and aldehydes in which the aldehyde group is on an aromatic ring. This combination of at least two aldehydes is described in more detail in International Patent Application Pub. No. WO 00/49120.

As used herein, the term "reactive aldehydes" further encompasses deodorizing materials that are the reaction products of (i) an aldehyde with an alcohol, (ii) a ketone with an alcohol, or (iii) an aldehyde with the same or different aldehydes. Such deodorizing materials can be: (a) an acetal or hemiacetal produced by means of reacting an aldehyde with a carbinol; (b) a ketal or hemiketal produced by means of reacting a ketone with a carbinol; (c) a cyclic triacetal or a mixed cyclic triacetal of at least two aldehydes, or a mixture of any of these acetals, hemiacetals, ketals, hemiketals, or cyclic triacetals. These deodorizing perfume materials are described in more detail in International Patent Application Pub. No. WO 01/07095.

In another embodiment, flavanoids can be used as an odor control agent. Flavanoids are compounds based on the C6-C3-C6 flavan skeleton. Flavanoids can be found in typical essential oils. Such oils include essential oil extracted by dry distillation from needle leaf trees and grasses such as cedar, Japanese cypress, eucalyptus, Japanese red pine, dandelion, low striped bamboo and cranesbill and can contain terpenic material such as alpha-pinene, beta-pinene, myrcene, phencone and camphene. Also included are extracts from tea leaf. Descriptions of such materials can be found in JP 02284997 and JP 04030855.

Zeolites

The odor control agents herein can also be zeolites. A preferred class of zeolites is characterized as "intermediate" silicate/aluminate zeolites. The intermediate zeolites are characterized by $SiO_2/AlO_2$ molar ratios of less than about 10. Preferably the molar ratio of $SiO_2/AlO_2$ ranges from about 2 to about 10. The intermediate zeolites can have an advantage over the "high" zeolites. The intermediate zeolites have a higher affinity for amine-type odors, they are more weight efficient for odor absorption because they have a larger surface area, and they are more moisture tolerant and retain more of their odor absorbing capacity in water than the high zeolites. A wide variety of intermediate zeolites suitable for use herein are commercially available as Valfor® CP301-68, Valfor® 300-63, Valfor® CP300-35, and Valfor® CP300-56, available from PQ Corporation, and the CBV100® series of zeolites from Conteka.

Zeolite materials marketed under the trade name Abscents® and Smellrite®, available from The Union Carbide Corporation and UOP are also preferred. Such materials are preferred over the intermediate zeolites for control of sulfur-containing odors, e.g., thiols, mercaptans.

When zeolites are used as odor control agents in compositions that are to be sprayed onto surfaces, the zeolite material preferably has a particle size of less than about 10 microns and is present in the composition at a level of less than about 1% by weight of the composition.

Activated Carbon

Activated carbon is another suitable odor control agent or incorporation in the present compositions. The carbon material suitable for use in the present invention is the material well known in commercial practice as an absorbent for organic molecules and/or for air purification purposes. Often, such carbon material is referred to as "activated" carbon or "activated" charcoal. Such carbon is available from commercial sources under such trade names as; Calgon-Type CPG®; Type PCB®; Type SGL®; Type CAL®; and Type OL®.

When activated carbon is used as an odor control agent in compositions that are to be sprayed onto surfaces, the activated carbon preferably has a particle size of less than about 10 microns and is present in the composition at a level of less than about 1% by weight of the composition.

To the extent any material described herein as an odor control agent might also be classified as another component described herein, for purposes of the present invention, such material shall be classified as an odor control agent.

In one embodiment, the composition further comprises one or more antioxidant. In one embodiment, the one or more antioxidant is selected from one or more of a group consisting of ascorbic acid and salts thereof, tocopherol and its derivatives, butyl hydroxyanisole (BHA), butyl hydroxytoluene (BHT), erythorbic acid, propyl gallate, sodium erythorbate, tertiary butyl hydroquinone (TBHQ) and rosemary.

As a co-solvent may contribute to the total VOC content of the composition, the presence of a co-solvent in the aerosol composition is optional and preferably in amount of no more than about 40 wt %, and preferably at a concentration lower than the water content. In a preferred embodiment, no solvent is present and, thus, an emulsifier is required to be present in an amount of from about 0.4 to about 4 wt % to insure formation of the desired emulsion. On the other hand, the emulsifier content may be reduced if a co-solvent is utilized. In one embodiment, the air treating composition does not include any emulsifier.

Aerosol Propellants

Wherein the present compositions are in the form of an aerosol spray composition, the compositions further comprise an aerosol propellant. Non-limiting examples of suitable aerosol propellants for aerosol compositions herein include aliphatic hydrocarbons such as butane, isobutane, and propane; low molecular weight halogenated hydrocarbons (preferably chlorinated and/or fluorinated hydrocarbons) such as chlorodifluoromethane; dissolvable gases such as carbon dioxide; nitrogen gas; compressed air; and other materials well known in the art.

When present, aerosol propellants are typically incorporated in the present compositions at a level of from about 2% to about 60%. preferably from about 3% to about 50%, by weight of the composition.

In one embodiment, the aerosol compositions have a volatile organic content (VOC) of less than 5.0% as to the total composition based on 100 wt. %. In one embodiment, the VOC content is less than 3.0% as to the total composition. In one embodiment, the VOC content is less than 1.0%.

In one embodiment, the compressed gas is included in an amount of about 5 to about 70 wt. %, preferably about 10 to about 60 wt. %, and most preferably about 20 to about 50 wt. %. The compressed gas propellant is useful in the stated amounts for providing a suitable particle size and spray rate over the life of the product when the pressure within the container is sufficient to provide an acceptable spray.

Compressed gases suitable for use in the compositions of the present invention include are, for example, nitrogen, air, carbon dioxide, nitrous oxide, inert gases, and mixtures thereof. In one embodiment, the propellants useful in the present invention are non-hydrocarbons.

The compositions of the present invention may comprise additional additives in any combination thereof, as long as the effect of the deodorizer against odor of the present invention is maintained.

Microcapsules Containing an Active Material

The malodor-controlling compositions of the present invention may optionally comprise microcapsules containing an active material and/or an optional odor control agent (which may be referred to herein as an "encapsulated odor control agent"), and/or an odor control agent outside of the microcapsules, and aqueous carrier.

It should be understood that the encapsulated odor control agent need not be completely encapsulated (that is, in some embodiments, it may be partially encapsulated). The same is true for the microcapsules containing the active material.

There are a non-limiting number of embodiments of the compositions described herein. These embodiments include, but are not limited to embodiments in which at least some of the same microcapsules contain both an active material and the optional odor control agent therein. In other embodiments, the composition may comprise a group of microcapsules that contain an active material, and different microcapsules that contain the optional odor control agent. The composition may comprise microcapsules with different types of shells or coating materials. In addition, in some embodiments, the encapsulated odor control agent and the odor control agent outside of the microcapsules may be the same odor control agent. In other embodiments, they may be different odor control agents.

The present compositions can also contain a wide variety of additional optional ingredients such as dispersants, solvents, aerosol propellants, surfactants, free perfume, antimicrobial actives/preservatives, wrinkle control agents, and the like. The compositions can be used to reduce or remove malodor from surfaces (especially fabrics) and provide a controlled-release of the active material. When the active material is a perfume, the present compositions provide a controlled-release scent.

The present compositions comprise microcapsules containing an active material and/or an optional odor control agent. The microcapsules provide a controlled-release of the active material and/or an optional odor control agent contained in the microcapsule. The microcapsules in the compositions of the present invention can be any ruptureable capsule containing an active material therein and/or an optional odor control agent or capsule which is controllably penetrable by the active material or odor control agent encapsulated therein. The rupture strength of the microcapsules should be within a range that can endure handling and spraying without rupturing and yet break by applying a force of friction across the surface being treated with the composition.

The shell of the microcapsules can be made from a wide variety of materials. Such materials are typically polymeric and are designed to resist becoming solubilized in the chemical matrix of the present compositions. Non-limiting examples of materials suitable for making the shell of the microcapsules herein include urea-formaldehydes, melamineformaldehydes, phenolformaldehydes, gelatin, poly(vinyl alcohol), poly(vinyl pyrrolidone), polyacrylates, polyamides, polyurethane, polymethacrylates, polyepoxides, cellulose acetate, cellulose nitrate, cellulose acetate butyrate, ethyl cellulose polyester, polychlorotrifluoroethylene (e.g. KEL-F), ethyl/vinyl acetate, saran, polystyrene, zein, paraffin wax, animal wax, vegetable wax, microcrystalline wax, polyethylene wax, and the like. Preferred microcapsule shell materials include poly(oxymethyleneurea), poly(oxymethylenemelamine), gelatin, polyurethane, poly(vinyl alcohol), and mixtures thereof. Other suitable microcapsule shell materials are disclosed in, e.g., U.S. Pat. Nos. 2,800,458; 3,159,585; 3,516,846; 3,533,958; 3,697,437; 3,888,689; 3,996,156; 3,965,033; 4,010,038; 4,016,098; 4,087,376; 5,591,146; UK Patent Nos. 2,006,709 and 2,062,570; and Benita, Simon (ed.), MICROENCAPSULATION: METHODS AND INDUSTRIAL APPLICATIONS (Marcel Dekker, Inc. 1996).

The size of the microcapsules can be important in the usefulness of microcapsules according to the practice of the present invention. Generally, the microcapsules will have an average diameter of from about 0.001 to about 1,000 microns, preferably from about 1 to about 500 microns, more preferably from about 10 to about 100 microns, and even more preferably from about 20 to about 70 microns. These dimensions can play an important role in the ability to control the application of capsules in the practice of the present invention. The broadest range of capsule size under any conditions would be about 0.001 to about 1,000 microns and a more easily sprayed size limit would be between about 20 and about 70 microns.

In general, the present compositions can comprise microcapsules at a wide variety of levels. Microcapsules are typically included in the present compositions at a level of from about 0.001% to about 99.9%, preferably from about 0.005% to about 50%, and more preferably from about 0.01% to about 20%, by weight of the composition. When the compositions are aqueous liquid compositions (especially non-aerosol compositions) to be sprayed onto surfaces, such as fabrics, the compositions will preferably comprise less than about 1%, preferably less than about 0.9%, more preferably less than about 0.5%, and even more preferably less than about 0.2%, by weight of the composition, of microcapsules. If the level of microcapsules is too high, the compositions may leave a visible residue on the surface being treated. In addition, if the surface is fabric and the level of microcapsules is too high, the fabric appearance may be altered. Furthermore, if the active material is perfume and the level of microcapsules is too high, the initial perfume "burst" when the product is sprayed onto the surface may be unpleasant to the consumer, since the force of the spray tends to rupture some of the microcapsules.

A variety of processes known in the art can be used to make the microcapsules herein. Examples of processes for making microcapsules are described in U.S. Pat. Nos. 2,800,458; 3,159,585; 3,516,846; 3,516,941; 3,533,958; 3,697,437; 3,778,383; 3,888,689; 3,965,033; 3,996,156; 4,010,038; 4,016,098; 4,087,376; 4,089,802; 4,100,103; 4,251,386; 4,269,729; 4,303,548; 4,460,722; and 4,610,927; UK Patent Nos. 1,156,725; 1,483,542; 2,041,319 and 2,048,206; and Benita, Simon (ed.), MICROENCAPSULATION: METHODS AND INDUSTRIAL APPLICATIONS (Marcel Dekker, Inc. 1996).

The active material can be a wide variety of materials in which one would want to deliver in a controlled-release manner onto the surfaces being treated with the present compositions or into the environment surrounding the surfaces. Non-limiting examples of active materials include perfumes, flavoring agents, fungicide, brighteners, antistatic agents, wrinkle control agents, fabric softener actives, hard surface cleaning actives, skin and/or hair conditioning agents, antimicrobial actives, UV protection agents, insect repellants, animal/vermin repellants, flame retardants, and the like.

In a preferred embodiment, the active material is a perfume, in which case the microcapsules containing perfume provide a controlled-release scent onto the surface being treated or into the environment surrounding the surface. In this case, the perfume can be comprised of a number of perfume raw materials known in the art, such as essential oils, botanical extracts, synthetic perfume materials, and the like.

In general, the active material is contained in the microcapsule at a level of from about 1% to about 99%, preferably from about 10% to about 95%, and more preferably from about 30% to about 90%, by weight of the total microcapsule. The encapsulated odor control agent, if present may be contained in microcapsules at the same range of levels. Of course if both active material and an odor control agent are contained in the same microcapsule, the total percentage of these components will never exceed 100%. The weight of the total microcapsule includes the weight of the shell of the microcapsule plus the weight of the material inside the microcapsule.

Antimicrobial Agents

One or more antimicrobial agents may be used in the antimicrobial compositions at a suitable level to produce the desired antimicrobial activity. Antimicrobial agents are typically present in a total amount greater than 1 wt. %, preferably in an amount greater than 5 wt. %, more preferably in an amount greater than 8 wt. %, relative to the total weight of the antimicrobial composition. In a preferred embodiment, the antimicrobial acid are present in a total amount of no greater than 20 wt. %, or 15 wt-%, based on the total weight of the composition.

Antibiotics and antimicrobials that may be used include one or more of benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as scymnol sulfate and its derivatives, deoxycholate and cholate.

The antimicrobial agent may comprise an antimicrobial organic acid, which includes soluble and stable alpha-hydroxy acids, beta-hydroxy acids, other carboxylic acids, including a (C2-C6) saturated or unsaturated alkyl carboxylic acid, a (C6-C16) aryl carboxylic acid, a (C6-C16) aralkyl carboxylic acid, a (C6-C12) alkaryl carboxylic acid, or oligomers that degrade to release one of the above organic acids. Examples of such oligomers are oligomers of glycolic acid, lactic acid or both having at least 4 or 6 repeat units. Various combinations of antimicrobial acids can be used if desired.

The alpha-hydroxy acid, beta-hydroxy acid, and other carboxylic acid antimicrobial acid are preferably present in their protonated, free acid form. It is not necessary for all of the antimicrobial acids to be present in the free acid form; however, the preferred concentrations listed below refer to the amount present in the free acid form. Although less preferred, the conjugate bases, e.g. alkali-, alkali-earth and ammonium salts, may be used provided they provide a homogenous mixture with the carrier. In some embodiments the antimicrobial acids may be substituted with one or more halogen atoms. Additional, non-alpha hydroxy acid, beta-hydroxy acid or other carboxylic acid antimicrobial acids, may be added in order to acidify the formulation or buffer it at a pH to maintain antimicrobial activity. Preferably, acids are used having a pKa greater than about 2.5, preferably greater than about 3, and most preferably greater than about 3.5.

Exemplary alpha-hydroxy acids include, but are not limited to, lactic acid, malic acid, citric acid, 2-hydroxybutanoic acid, mandelic acid, gluconic acid, glycolic acid, tartaric acid, ascorbic acid, alpha-hydroxyoctanoic acid, and hydroxycaprylic acid, as well as derivatives thereof (e.g., compounds substituted with hydroxyls, phenyl groups, hydroxyphenyl groups, alkyl groups, halogens, as well as combinations thereof). Preferred alpha-hydroxy acids include lactic acid, glycolic acid, malic acid, and mandelic acid. These acids may be in D, L, or DL form and may be present as free acid, salts, or partial salts thereof. All such forms are encompassed by the term "acid." Preferably, the acids are present in the free acid form. Other suitable alpha-hydroxy acids are described in U.S. Pat. No. 5,665,776 (Yu).

Exemplary beta-hydroxy acids include, but are not limited to, salicylic acid, beta-hydroxybutanoic acid, tropic acid, and trethocanic acid. In certain preferred embodiments, the beta-hydroxy acids useful in the compositions of the present invention are selected from the group consisting of salicylic acid, beta-hydroxybutanoic acid, and mixtures thereof. Other suitable beta-hydroxy acids are described in U.S. Pat. No. 5,665,776.

Carboxylic acids other than alpha- and beta-carboxylic acids are also suitable antimicrobial acids. They include alkyl, aryl, aralkyl, or alkaryl carboxylic acids typically having equal to or less than 12 carbon atoms. The carboxylic acid may be a (C2-C6) alkyl carboxylic acid, a (C6-C16) aralkyl carboxylic acid, or a (C6-C16) alkaryl carboxylic acid. Exemplary acids include, but are not limited adipic acid, sorbic acid, benzoic acid, benzylic acid, and nonylbenzoic acid.

Despite the presence of the antimicrobial acid and fatty alcohol in the antimicrobial compositions, little esterification of the components is observed, even when applied from the melt. It has been observed that less than 1 wt. % of ester is observed after ageing at 40° C. for a day.

Alternatively the antimicrobial agent may comprise cationic amine antimicrobial compounds, which include antimicrobial protonated tertiary amines, biguanidines and small molecule quaternary ammonium compounds.

Exemplary small molecule quaternary ammonium compounds include benzalkonium chloride and alkyl substituted derivatives thereof, di-long chain alkyl (C8-C18) quaternary ammonium compounds, cetylpyridinium halides and their derivatives, benzethonium chloride and its alkyl substituted derivatives, octenidine and compatible combinations thereof. Exemplary compounds within this class are: chlorohexidine gluconate, monoalkyltrimethylammonium salts, monoalkyldimethyl-benzyl ammonium salts, dialkyldimethyl ammonium salts, benzethonium chloride, alkyl substituted benzethonium halides such as methylbenzethonium chloride and octenidine.

Additional examples of quaternary ammonium antimicrobial agents are: benzalkonium halides having an alkyl chain length of C8-C18, preferably C12-C16, more preferably a mixture of chain lengths, e.g., benzalkonium chloride comprising 40% C1-2 alkyl chains, 50% C1-4 alkyl chains, and 10% C16 chains (available as Barquat MB-50 from Lonza Group Ltd.); benzalkonium halides substituted with alkyl groups on the phenyl ring (available as Barquat 4250); dimethyldialkylammonium halides having C8-C18 alkyl groups, or mixtures of such compounds (available as Bardac 2050, 205M and 2250 from Lonza); and cetylpyridinium halides such as cetylpyridinium chloride (available as Cepacol Chloride from Merrell Labs); benzethonium halides and alkyl substituted benzethonium halides (available as Hyamine 1622 and Hyamine 10× from Rohm and Haas). Useful protonated tertiary amines have at least one C6-C18 alkyl group.

The antimicrobial agent may comprise a biguanidine, including polybiguanidine, compounds. An exemplary compound of this class is polyhexamethylene biguanide (PHMB) commercially available as Cosmocil CQ from Aveci, Wilmington, Del.

Specific examples of these compounds include, but are not limited to, polyhexamethylene biguanide hydrochloride, p-chlorophenyl biguanide; and A-chlorobenzhydryl biguanide. In another aspect of this embodiment, the biguanide compounds include, but are not limited to, halogenated hexidine such as, but not limited to, chlorhexidine (1,1'-hexamethylene-bis-5-(4-chlorophenyl biguanide) and its salts. One particularly suitable biguanide is polyhexamethylenebiguanide hydrochloride The antimicrobial agent may comprise a phenolic compound. Examples of phenolic agent include, but are not limited to, butylated hydroxy anisole, e.g., 3(2)-tert-butyl-4-methoxyphenol (BHA), 2,6-di-tert-butyl-4-methylphenol (BHT), 3,5-di-tert-butyl-4-hydroxybenzylphenol, 2,6-di-tert-4-hexylphenol, 2,6-di-tert-4-octylphenol, 2,6-di-tert-4-decylphenol, 2,6-di-tert-butyl-4-ethylphenol, 2,6-di-tert-4-butylphenol, 2,5-di-tert-butylphenol, 3,5-di-tert-butylphenol, 4,6-di-tert-butyl-resorcinol, methyl paraben (4-hydroxybenzoic acid methyl ester), ethyl paraben, propyl paraben, butyl paraben, 2-phenoxyethanol, as well as combinations thereof. One group of the phenolic compounds is the phenol species having the general structure shown above where R25 is H and where R24 is alkyl or alkenyl of up to 8 carbon atoms, and n is 0, 1, 2, or 3, especially where at least one R24 is butyl and particularly tert-butyl, and especially the non-toxic members thereof being preferred. Some of the phenolic synergists are BHA, BHT, methyl paraben, ethyl paraben, propyl paraben, and butyl paraben as well as combinations of these.

Other additional antimicrobial agents include iodine and its complexed forms such as povidone/rodine, chlorhexidine salts such as chlorhexidine digluconate (CHG), parachlorometaxylenol (PCMX), triclosan, hexachlorophene, surfactants having a C12-C22 hydrophobe and a quaternary ammonium group, quaternary amines, quaternary silanes, hydrogen peroxide, silver, silver salts such as silver chloride, silver oxide, silver sulfadiazine, and the like.

For skin contact articles, suitable optional carrier materials include emollients and humectants such as those described in U.S. Pat. No. 5,951,993. In addition, emollients such as oils (for example, hydrocarbons and alkyl esters) and skin acceptable alkyl alcohols and polyethoxylated alcohols, and combinations thereof, also may improve the skin feel of the coated articles. Any indicator that provides a visual change in response to the absence or presence of a specific compound or compounds, such as, water, urea, dissolved oxygen, ions, such as, but not limited to, iron, calcium, magnesium, zinc, sodium, chloride, protons, hydroxide and combinations thereof, sugars, such as, glucose, enzymes, biological materials in the urine and/or feces; and combinations thereof, microbiological flora and fauna, such as, bacteria and the like; some threshold level of a compound or composition, such as, water, urine etc., below a certain amount; and combinations thereof, may be included in the antimicrobial composition. Embodiments of visual indicators include those that change color, color intensity, or change between colorless and colored, or between transparent, translucent and opaque. In particular, color or moisture indicators that provide a color change may be included.

Wrinkle Control Agents

The present compositions can optionally further comprise a wrinkle control agent, wherein the wrinkle control agent helps to prevent and/or control wrinkles from forming in surfaces treated with the present compositions, especially fabrics. Wrinkle control agents useful herein include fiber lubricant, shape retention polymer, hydrophilic plasticizer, lithium salt, and mixtures thereof. Such wrinkle control agents are described in detail in U.S. Pat. No. 6,001,343 issued Dec. 14, 1999 to Trinh et al. Wrinkle control compositions that can be suitable as base compositions of the present invention that comprise microcapsules containing an active material, especially compositions that can be used in a cabinet-type or bag-type apparatus for conditioning garments, are also disclosed in co-pending U.S. application Ser. No. 09/674,224 filed Apr. 27, 1998 by Hubesch et al. (which relates to WO 99/55950 published Nov. 4, 1999); and co-pending U.S. application Ser. No. 09/673,600 filed Apr. 27, 1998 by Woo et al. (which relates to WO 99/55816 published Nov. 4, 1999).

Methods of Use

The malodor control composition of the present invention may be used in a wide variety of applications to neutralize malodors in the air or on inanimate surface by contacting a malodor with effective amounts of the composition. In some embodiments, the malodor control composition may be formulated for use in energized vapor phase systems. "Energized" as used herein refers to a system that operates by using an electrical energy source, such as a battery or electrical wall outlet, to emit a targeted active.

In some embodiments, the malodor control composition may be formulated for use in non-energized vapor phase systems. "Non-energized" as used herein refers to a system that emits a targeted active passively or without the need for an electrical energy source. Aerosol sprayers and traditional trigger/pump sprayers are considered non-energized systems. Non-limiting examples of a non-energized vapor phase system are passive air freshening diffusers and aerosol sprays such as fabric and air freshening sprays and body deodorants.

In other embodiments, the malodor control composition may be formulated for use in a liquid phase system. Non-limiting examples of a liquid phase system are liquid laundry products such as laundry detergents and additives; dish detergents; personal hygiene products such as body washes, shampoos, and conditioners.

The malodor control composition may also be formulated for use in substrates such as plastics, wovens, or non-wovens (e.g. cellulose fibers for paper products). Such substrates may be used as pet food packaging; paper towels; tissues; trash bags; diapers; baby wipes; adult incontinence products; feminine hygiene products such as sanitary napkins and tampons. The malodor control composition may also be formulated for use in commercial or industrial systems such as in septic tanks or sewage treatment equipment.

The use of the compounds of the present invention is applicable in perfumery products, including the preparations of perfumes and colognes, the perfuming of personal care products such as soaps, shower gels, and hair care products, fabric care products, air fresheners, and cosmetic preparations. The present invention can also be used to perfume cleaning agents, such as, but not limited to detergents, dishwashing materials, scrubbing compositions, window cleaners and the like. In these preparations, the compounds of the present invention can be used alone or in combination with other perfuming compositions, solvents, adjuvants and the like. Those with skill in the art know the nature and variety of the other ingredients that can also be employed.

A list of suitable fragrances is provided in U.S. Pat. No. 4,534,891, the contents of which are incorporated by reference as if set forth in its entirety. Another source of suitable fragrances is found in Perfumes, Cosmetics and Soaps, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The compounds of the present invention can be used in combination with a complementary fragrance compound. The term "complementary fragrance compound" as used herein is defined as a fragrance compound selected from the group consisting of 2-[(4-methylphenyl)methylene]-heptanal (Acalea), iso-amyl oxyacetic acid allylester (Allyl Amyl Glycolate), (3,3-dimethylcyclohexyl)ethyl ethyl propane-1, 3-dioate (Applelide), (E/Z)-1-ethoxy-1-decene (Arctical), 2-ethyl-4-(2,2,3-trimethyl-3-cyclo-penten-1-yl)-2-buten-1-ol (Bacdanol), 2-methyl-3-[(1,7,7-trimethylbicyclo[2.2.1] hept-2-yl)oxy]exo-1-propanol (Bornafix), 1,2,3,5,6,7-hexahydro-1,1,2,3,3-pentamethyl-4H-inden-4-one (Cashmeran), trimethylcyclopentenylmethyloxabicyclooctane (Cassiffix), 1,1-dimethoxy-3,7-dimethyl-2,6-octadiene (Citral DMA), 3,7-dimethyl-6-octen-1-ol (Citronellol), 3A,4,5,6,7,7A-hexahydro-4,7-methano-1H-inden-5/6-yl acetate (Cyclacet), 3A,4,5,6,7,7A-hexahydro-4,7-methano-1H-inden-5/6-yl propinoate (Cyclaprop), 3A,4,5,6,7,7A-hexahydro-4,7-methano-1G-inden-5/6-yl butyrate (Cyclobutanate), 1-(2,6,6-trimethyl-3-cyclohexen-1-yl)-2-buten-1-one (Delta Damascone), 3-(4-ethylphenyl)-2,2-dimethyl propanenitrile (Fleuranil), 3-(O/P-ethylphenyl) 2,2-dimethyl propionaldehyde (Floralozone), tetrahydro-4-methyl-2-(2-methylpropyl)-2H-pyran-4-ol (Floriffol), 1,3,4,6,7,8-hexahydro-4,6,6, 7,8,8-hexamethylcyclopenta-gamma-2-benzopyran (Galaxolide), 1-(5,5-dimethyl-1-cyclohexen-1-yl)pent-4-en-1-one (Galbascone), E/Z-3,7-dimethyl-2,6-octadien-1-yl acetate (Geranyl Acetate), alpha-methyl-1,3-benzodioxole-5-propanal (Helional), 1-(2,6,6-trimethyl-2-cyclohexen-1-yl)-1,6-heptadien-3-one (Hexalon), (Z)-3-hexenyl-2-hydroxybenzoate (Hexenyl Salicylate, CIS-3), 4-(2,6,6-trimethyl-2-cyclohexen-1-yl)-3-buten-2-one (Ionone a), 1-(1,2,3,4,5,6,7,8-octahydro-2,3,8,8-tetramethyl-2-naphthalenyl)-ethan-1-one (Iso E Super), methyl 3-oxo-2-pentylcyclopentaneacetate (Kharismal), 2,2,4-trimethyl-4-phenylbutanenitrile (Khusinil), 3,4,5,6,6-pentamethylhept-3-en-2-one (Koavone), 3/4-(4-hydroxy-4-methyl-pentyl) cyclohexene-1-carboxaldehyde (Lyral), 3-methyl-4-(2,6,6-trimethyl-2-cyclohexen-1-yl)-3-buten-2-one (Methyl Ionone y), 1-(2,6,6-trimethyl-2-cyclohexen-1-yl) pent-1-en-3-one (Methyl Ionone a Extra, Methyl Ionone N), 3-methyl-4-phenylbutan-2-ol (Muguesia), cyclopentadec-4-en-1-one (Musk Z4), 3,3,4,5,5-pentamethyl-11,13-dioxatricyclo [7.4.0.0<2,6>]tridec-2(6)-ene (Nebulone), 3,7-dimethyl-2, 6-octadien-1-yl acetate (Neryl Acetate), 3,7-dimethyl-1,3,6-octatriene (Ocimene), ortho-tolylethanol (Peomosa), 3-methyl-5-phenylpentanol (Phenoxanol), 1-methyl-4-(4-methyl-3-pentenyl) cyclohex-3-ene-1-carboxaldehyde (Precyclemone B), 4-methyl-8-methylene-2-adamantanol (Prismantol), 2-ethyl-4-(2,2,3-trimethyl-3-cyclopenten-1-yl)-2-buten-1-ol (Sanjinol), 2-methyl-4-(2,2,3-trimethyl-3-cyclopenten-1-yl)-2-buten-1-ol (Santaliff), Terpineol, 2,4- dimethyl-3-cyclohexene-1-carboxaldehyde (Triplal), decahydro-2,6,6,7,8,8-hexamethyl-2H-indeno[4,5-B]furan (Trisamber), 2-tert-butylcyclohexyl acetate (Verdox), 4-tert-butylcyclohexyL acetate (Vertenex), acetyl cedrene (Vertofix), 3,6/4,6-dimethylcyclohex-3-ene-1-carboxaldehyde (Vertoliff), and (3Z)-1-[(2-methyl-2-propenyl)oxy]-3-hexene (Vivaldie).

The fragrance formulation of the present invention is a consumer composition comprising a compound of the present invention. The fragrance formulation of the present invention may comprise a compound under the trademark of AROMACOTE (Bell Flavors & Fragrances, Inc.) of the present invention and further a complementary fragrance compound as defined above.

The amount of the compounds of the present invention employed in a fragrance formulation varies from about 0.005 to about 70 weight percent, preferably from 0.05 to about 50 weight percent, more preferably from about 0.5 to about 25 weight percent, and even more preferably from about 1 to about 10 weight percent. Those with skill in the art will be able to employ the desired amount to provide desired fragrance effect and intensity. In addition to the compounds of the present invention, other materials can also be used in conjunction with the fragrance formulation to encapsulate and/or deliver the fragrance. Some well-known materials are, for example, but not limited to, polymers, oligomers, other non-polymers such as surfactants, emulsifiers, lipids including fats, waxes and phospholipids, organic oils, mineral oils, petrolatum, natural oils, perfume fixatives, fibers, starches, sugars and solid surface materials such as zeolite and silica.

When used in a fragrance formulation these ingredients provide additional notes to make a fragrance formulation more desirable and noticeable, and add the perception of value. The odor qualities found in these materials assist in beautifying and enhancing the finished accord as well as improving the performance of the other materials in the fragrance.

In addition, the compounds of the present invention are also surprisingly found to provide superior ingredient performance and possess unexpected advantages in malodor counteracting applications such as body perspiration, environmental odor such as mold and mildew, bathroom, and etc. The compounds of the present invention substantially eliminate the perception of malodors and/or prevent the formation of such malodors, thus, can be utilized with a vast number of functional products.

Examples of the functional products are provided herein to illustrate the various aspects of the present invention. However, they do not intend to limit the scope of the present invention. The functional products may include, for example, a conventional room freshener (or deodorant) composition such as room freshener sprays, an aerosol or other spray, fragrance diffusers, a wick or other liquid system, or a solid, for instance candles or a wax base as in pomanders and plastics, powders as in sachets or dry sprays or gels, as in solid gel sticks, clothes deodorants as applied by washing machine applications such as in detergents, powders, liquids, whiteners or fabric softeners, fabric refreshers, linen sprays, closet blocks, closet aerosol sprays, or clothes storage areas or in dry cleaning to overcome residual solvent notes on clothes, bathroom accessories such as paper towels, bathroom tissues, sanitary napkins, towelettes, disposable wash cloths, disposable diapers, and diaper pail deodorants, cleansers such as disinfectants and toilet bowl cleaners, cosmetic products such as antiperspirant and deodorants, general body deodorants in the form of powders, aerosols, liquids or solid, or hair care products such as hair sprays, conditioners, rinses, hair colors and dyes, permanent waves, depilatories, hair straighteners, hair groom applications such as pomade, creams and lotions, medicated hair care products containing such ingredients as selenium sulfide, coal tar or salicylates, or shampoos, or foot care products such as foot powders, liquids or colognes, after shaves and body lotions, or soaps and synthetic detergents such as bars, liquids, foams or powders, odor control such as during manufacturing processes, such as in the textile finishing industry and the printing industry (inks and paper), effluent control such as in processes involved in pulping, stock yard and meat processings, sewage treatment, garbage bags, or garbage disposal, or in product odor control as in textile finished goods, rubber finished goods or car fresheners, agricultural and pet care products such as dog and hen house effluents and domestic animal and pet care products such as deodorants, shampoo or cleaning agents, or animal litter material and in large scale closed air systems such as auditoria, and subways and transport systems.

Malodor counteracting effective amount is understood to mean the amount of the inventive malodor counteractant employed in a functional product that is organoleptically effective to abate a given malodor while reducing the combined intensity of the odor level, wherein the given malodor is present in air space or has deposited on a substrate. The exact amount of malodor counteractant agent employed may vary depending upon the type of malodor counteractant, the type of the carrier employed, and the level of malodor counteractancy desired. In general, the amount of malodor counteractant agent present is the ordinary dosage required to obtain the desired result. The skilled practitioner in the art knows such dosage. In a preferred embodiment, when used in conjunction with malodorous solid or liquid functional products, e.g., soap and detergent, the compounds of the present invention may be present in an amount ranging from about 0.005 to about 50 weight percent, preferably from about 0.01 to about 20 weight percent, and more preferably from about 0.05 to about 5 weight percent, and when used in conjunction with malodorous gaseous functional products, the compounds of the present invention may be present in an amount ranging from about 0.1 to 10 mg per cubic meter of air.

EXAMPLES

Example 1

A list of fragrance materials with low odor thresholds were tested and evaluated on cotton substrate for strength and substantively (fragrance adhering to fabric for extended length of time). The best performing materials were then individually applied at a concentration of 0.01 to 0.1% on a non-gel, non-scented diaper substrate and dried for three days. After three days the urine malodor was applied to the pretreated swatches. Each material was then evaluated for ability to cover the malodor without in turn giving off strong perfume odor. Those materials without odor blocking characteristics were eliminated and those generating stronger organoleptic detection after testing were also eliminated. The materials were rated by a team of perfumers from no odor to high impact. As some companies use iso-valeric acid as a target malodor, the MOC compound was also evaluated against iso-valeric acid (perspiration odor). As propionic acid (foot odor) and hexanoic acid (pet odor) are mentioned in the literature, they were also tested against these materials.

Gas chromatographic analysis using a polar column shows that the selected materials elute at the same intervals as the malodor components in the synthetic urine. This co-elution substantiates the organoleptic evaluation of the compound's ability to combine with malodors thus neutralizing or blocking the urine, iso-valeric acid, propionic acid and hexanoic acid malodors.

The methodology of evaluating the fecal odorants is the same as the urine, dynamic headspace GC-MS also called purge and trap GC-MS. A weighed amount of unfragranced diaper is placed in a 20 ml headspace vial and the appropriate solutions added. Solutions include a standard as a check of instrument performance, known amounts of the MOC formulation, and known amounts of either synthetic fecal (in house), or Surine™ Negative Urine Control (Item 720-1; Cerilliant Corporation, Round Rock, Tex.). Surine™ Negative Urine Control is rugged non-biological urine with constituents that mimic human urine without human urine's research impediments.

The vial is capped heated while the headspace is purged with nitrogen. The nitrogen passes through a collection tube filled with an appropriate adsorbent (e.g. PDMS, PEG). Volatile compounds are trapped on the adsorbent during the purging process. The tube is transferred to the injection port of the GC and desorbed. Analytes are carried through a GC column, which slowly heats up. Separation on the column is due to differences in boiling points and functional groups (acid, aldehyde) on the compound. The compounds are detected by the mass spectrometer where they can be identified.

Both materials are synthetic form of excreta, whose benefit is that it mimics the real substrate without any biohazard/safety concerns. Surine™ Negative Urine Control has odorants characterized by the above method. The fecal synth is an in-house formula developed for pet care technology. It is a combination of volatiles found in feces such as fatty acids, aromatics, and nitrogenous compounds. These compounds represent the metabolism of proteins and carbohydrate's by the organism. An internal standard (carvyl acetate) is added to monitor instrument performance. Dilutions, when necessary, are done using ethanol as it is not trapped during the purging process.

Figure 2:
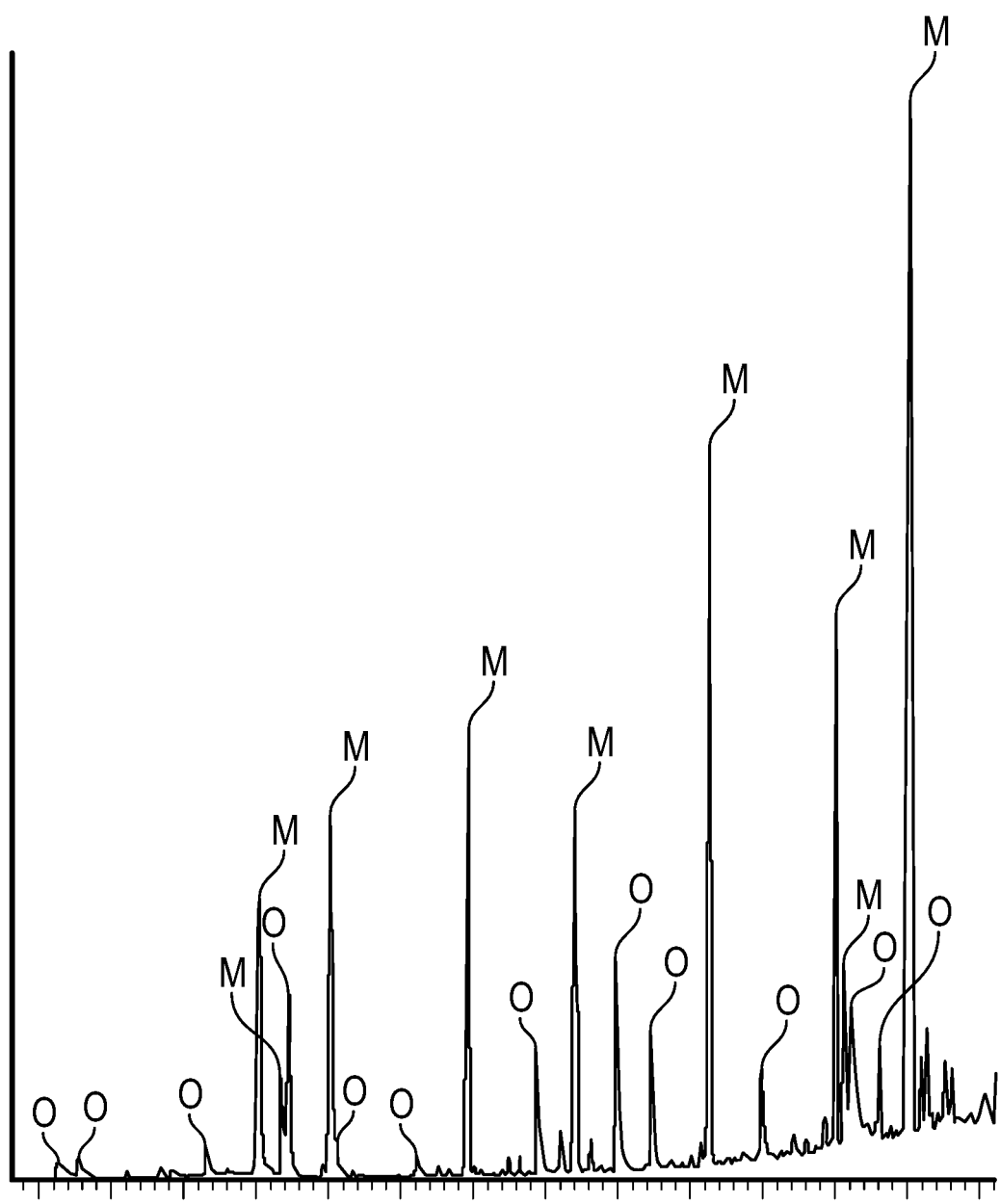
FIG. 2 illustrates gas chromatographic analyses showing that the Malodor Counteractant (MOC) materials elute at the same intervals as the malodor components in a synthetic urine, wherein "M" denotes products eluted from the Malodor Counteractant (MOC) materials and "O" denotes products eluted from the odorant; and wherein the figure depicts the elution of the malodor and the malodor counteractant (MOC) with carvyl acetate added as a marker.
Figure 3:
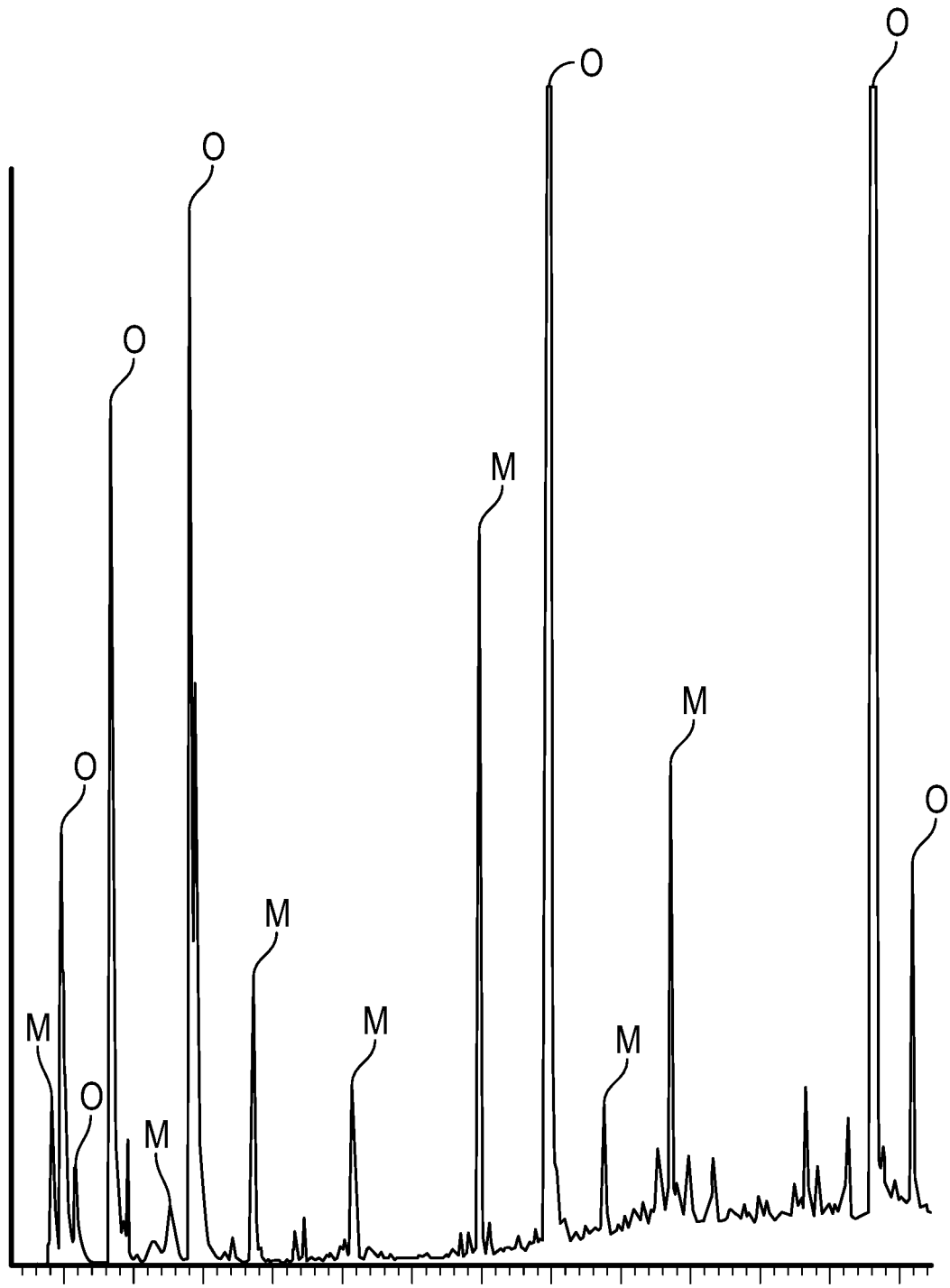
FIG. 3 illustrates gas chromatographic analyses showing that the Malodor Counteractant (MOC) materials elute at the same intervals as the malodor components in a synthetic feces, wherein "M" denotes products eluted from the Malodor Counteractant (MOC) materials and "O" denotes products eluted from the odorant; and wherein the figure depicts the elution of the malodor and the malodor counteractant (MOC) with carvyl acetate added as a marker.

The results are shown in FIGS. 1-3.

FIG. 1 illustrates gas chromatographic analyses showing products eluted from the odorant alone with carvyl acetate added as a control;

FIG. 2 illustrates gas chromatographic analyses showing that the Malodor Counteractant (MOC) materials elute at the same intervals as the malodor components in a synthetic urine, wherein "M" denotes products eluted from the Malodor Counteractant (MOC) materials and "O" denotes products eluted from the odorant; and wherein the figure depicts the elution of the malodor and the malodor counteractant (MOC) with carvyl acetate added as a control; and FIG. 3 illustrates gas chromatographic analyses showing that the Malodor Counteractant (MOC) materials elute at the same intervals as the malodor components in a synthetic feces, wherein "M" denotes products eluted from the Malodor Counteractant (MOC) materials and "O" denotes products eluted from the odorant; and wherein the figure depicts the elution of the malodor and the malodor counteractant (MOC) with carvyl acetate added as a control.

Example 2

Diaper Malodor Testing—Sample Preparation Protocol

Three days prior to evaluation, the Maxi Pads, fragrance, and urine are prepared for testing. Regular absorbency maxi pads with Flexi Wings-Stayfit with a Dri Silk Cover (UPC 11110351395; The Kroger Company) are provided.

1. Unwrap maxi pad from package and lie flat on counter;
2. Measure 3 inches from outside of both flaps to inside of pad and note with small ballpoint pen mark; with sharp scissors, cut both ends at mark; and
3. Take Maxi Pad ends and place one, absorbent side up, in 8 oz glass jar.

Fragrance Preparation 0.1% MOC solution:
1. Prepare Mixture 1: Mix 1 gram fragrance with 99 grams alcohol;
2. Prepare 0.1% MOC solution: Mix 1 gram Mixture 1 with 10 grams alcohol;
3. Apply 10 grams of 0.1% MOC solution of fragrance evenly across absorbent area of maxi pad swatch in jar;
4. Cover jars with lid and transfer to aging room; and
5. After placed in aging room, remove lids and allow fragranced maxi pads to age (dry) for 3 days Urine Preparation:
1. Add 40 grams Surine® odor to 1 liter of Surine® and thoroughly mix
2. Day of Evaluation treat with urine: Apply 8 mL of Surine® evenly across jarred maxi pad to mimic 45.7% saturation; and
3. Sit at room temperature for 3 minutes prior to evaluation.

Sensory Method Protocol: Sensory Methodology:
1. Expert Perfumers (n=4) evaluated maxi pads that were soiled with artificial urine and fragranced with the MOC (as prepared above).
2. After smelling the maxi pad, panelists rated Fragrance Intensity and Malodor Intensity, each on a 6 point category scale where 0=none and 5=very strong. The sample was presented blind and labeled with a 3-digit code.

Prior to the study, the Expert Perfumers aligned to a Reference sample for Very Strong Malodor Intensity (intensity level=5). The Reference sample was a soiled maxi pad without fragrance. There was no Reference sample for Fragrance Intensity.

Sensory Questionnaire regarding Fragrance Intensity
Q: How would you rate the Fragrance Intensity of this sample?
0—No Fragrance
1—Barely Noticeable Fragrance
2—Noticeable But Weak Fragrance
3—Moderate Fragrance
4—Strong Fragrance
5—Very Strong Fragrance Sensory Questionnaire regarding Malodor Intensity
Q; How would you rate the Malodor Intensity of this sample?
0—No Malodor
1—Slight, Barely Noticeable Malodor
2—Definite, Clearly Noticeable Malodor
3—Moderate Malodor
4—Strong Malodor
5—Very Strong Malodor The results are as follows:
Reference Malodor Intensity=5
Neutral 6121696 Malodor Intensity=0.75

The malodor starts at 100% or (5 out of 5), and when it is added to a diaper pretreated with the MOC compound, the average score of the professional panel rated it 0.75 meaning a 85% reduction in Malodor Intensity.

In repeated testing and optimizing the Malodor counteractant formula, and determining where it should be applied for commercial application and production revealed in repeated testing that 1 gram of the MOC formula removed 100% the odor of 500 grams of Surine® synthetic urine odor and actual human urine.

The Aromacote® Malodor Counteractant was able to reduce the malodor 85% against synthetic urine (Surnie with Urine malodor), against iso-valeric acid odorant, against hexanoic acid, and propionic acid.

Example 3

The effect of zinc ricinoleate [$Zn(Ri)_2$] on the partitioning of compounds into the headspace. Headspace analysis is a sampling technique in which a nonvolatile matrix (liquid or solid) is heated and volatiles are collected as they partition (migrate) into the unfilled volume of the vial (headspace). These compounds are concentrated on an adsorbent tube then injected into the chromatograph where individual compounds are separated.

A sample of volatile compounds are placed into a vial, sealed, and heated for a period of time. The volatile compounds will migrate into the gas headspace. The more volatile the compound, the more concentrated it will be in the headspace. Conversely, the less volatile components will partition into the headspace to a lesser extent thus separating components of interest from the nonvolatile sample matrix (diaper).

For each test compound, 1 microliter of a 100 nanogram/microliter (ng/µl) solution (100 ng of each fragrance chemical) is put into a vial, warmed, purged, and volatiles concentrated in an adsorbent cartridge. The cartridge is desorbed into the GC where individual compounds are separated. A second set of each of the fragrance chemicals is prepared and added to a vial where 0.5 g zinc ricinoleate has been added. Prior to the addition of the fragrance compound zinc ricinoleate was added to the vile, melted, and allowed to cool forming a thin film on the bottom of the vial to which each fragrances chemical was added. Vials were sealed and processed as outlined above.

Figure 4:
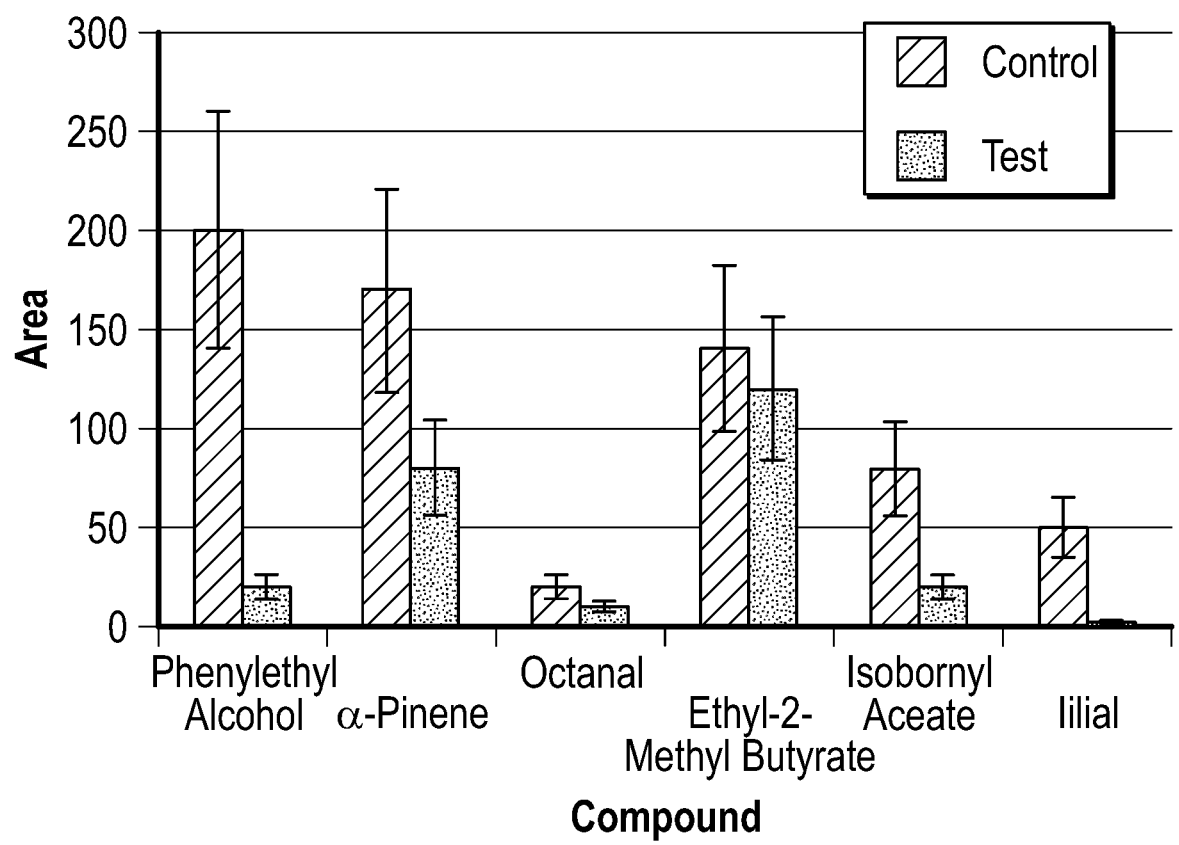
FIG. 4 illustrates gas chromatographic headspace measurements of fragrance compounds with and without Zinc Ricinoleate [Zn(Ri)$_2$]; wherein the results are shown for phenethylamine (PEA, β-phenylethylamine), α-pinene, octanal, E-2-M butyrate, isobornyl acetate, and lilial; wherein the first bar of each of the fragrance chemicals is the chemical itself and the second bar is the reduction of volatility caused by the addition of zinc ricinoleate on that chemical. An olfactive evaluation by a panel of perfumers showed a change in character of the fragrance materials caused by the zinc ricinoleate.

FIG. 4 illustrates gas chromatographic headspace measurements of fragrance compounds with and without Zinc Ricinoleate [$Zn(Ri)_2$]; wherein the results are shown for phenethylamine (PEA, β-phenylethylamine), α-pinene, octanal, E-2-M butyrate, isobornyl acetate, and lilial; wherein the first bar of each of the fragrance chemicals is the chemical itself and the second bar is the reduction of volatility caused by the addition of zinc ricinoleate on that chemical. Before the analysis, perfumers also compared the two samples by nose. The perfumers noted not only a reduction in strength but also a change in the character of each fragrance chemical when zinc ricinoleate is added. Therefore, it is shown that the zinc ricinoleate not only reduces fragrance strength but also it's character.

All publications, patents and patent applications cited herein, whether supra or infra, are hereby incorporated by reference in their entirety to the same extent as if each individual publication, patent or patent application was specifically and individually indicated as incorporated by reference. It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

It must be noted that, as used in this specification and the appended claims, the singular forms "a," "an" and "the" include plural referents unless the content clearly dictates otherwise. Thus, for example, reference to a "colorant agent" includes two or more such agents.

Unless defined otherwise, all technical and scientific terms used herein have the same meaning as commonly understood by one of ordinary skill in the art to which the invention pertains. As will be appreciated by one having ordinary skill in the art, the methods and compositions of the invention substantially reduce or eliminate the disadvantages and drawbacks associated with prior art methods and compositions.

It should be noted that, when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

While it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments, which come within the spirit and scope of the present invention.

What is claimed is:

1. A malodor counteractant composition comprising a malodor counteracting effective amount of a mixture of: propanedioic acid 1-(3,3-dimethylcyclohexyl)ethyl ethyl ester (CAS #478695-70-4); diphenyl oxide (CAS #101-84-8); 4-isopropylcyclohexanol (CAS #4621-04-9); and 2-phenoxyethyl-2-methylpropanoate (CAS #103-60-6); wherein the the mixture of the four ingredients works synergistically as a malodor counteractant composition.

2. The malodor counteractant composition of claim 1, wherein the malodor control composition comprises (a) from 1 to 35 wt. % propanedioic acid 1-(3,3-dimethylcyclohexyl)ethyl ethyl ester (CAS #478695-70-4); (b) from 1 to 35 wt. % diphenyl oxide; (c) from 1 to 35 wt. % 4-isopropylcyclohexanol (CAS #4621-04-9); and (d) from 5 to 90 wt. % 2-phenoxyethyl-2-methylpropanoate (CAS #103-60-6).

3. The malodor counteractant composition of claim 1, wherein the malodor control composition comprises (a) from 5 to 20 wt. % propanedioic acid 1-(3,3-dimethylcyclohexyl)ethyl ethyl ester (CAS #478695-70-4); (b) from 5 to 20 wt. % diphenyl oxide; (c) from 5 to 20 wt. % 4-isopropylcyclohexanol (CAS #4621-04-9); and (d) from 20 to 60 wt. % 2-phenoxyethyl-2-methylpropanoate (CAS #103-60-6).

4. The malodor counteractant composition of claim 3, wherein the composition further comprises one or more additional ingredients selected from the group consisting of 2-phenoxyethanol (CAS #122-99-6), ethyl 10-undecenoate (CAS #692-86-4), 2-methylundecanal (CAS #110-41-8), Tricyclo(5.2.1.02,6)dec-3-enyl acetate (CAS #54830-99-8), and hexyl salicylate (CAS #6259-76-3).

5. The malodor counteractant composition of claim 3, wherein the composition further comprises 5% to 60% of two or more additional compounds selected from the group consisting of: 2-phenoxyethanol (CAS #122-99-6), ethyl 10-undecenoate (CAS #692-86-4), 2-methylundecanal (CAS #110-41-8), Tricyclo(5.2.1.02,6)dec-3-enyl acetate (CAS #54830-99-8), and hexyl salicylate (CAS #6259-76-3).

6. The malodor counteractant composition of claim 1, wherein the composition is used in fragrance formulas at a concentration of from about 10 ppm to about 1000 ppm.

7. The malodor counteractant composition of claim 1, wherein the composition is used as part of a fragrance formula or added to personal care products from 0.5% up to 20% based on weight percent.

8. The malodor counteractant composition of claim 1, wherein the composition is used as part of an absorbent article from 100 ppm up to 2.5% maximum.

9. The malodor counteractant composition of claim 1 wherein the composition further comprises one or more additional ingredients selected from the group consisting of at least one odor neutralizing agent; and at least one dispersant; at least one fragrance; at least one buffering system; and at least one surfactant.

10. The malodor counteractant composition of claim 9 wherein the at least one odor neutralizing agent is selected from the group consisting of zeolites, activated carbons, zinc salts, zinc oxides, cyclodextrins, fatty alcohol esters, aliphatic aldehydes, zinc ricinoleate actives, benzaldehyde, soyethyl morpholinium ethosulfate, a blend of polyhydroaromatic sulfonates, and lauryl methacrylate.

11. The malodor counteractant composition of claim 1 wherein the composition further comprises one or more additional ingredients selected from the group consisting of odor masking agents, odor blocking agents, and diluents.

\* \* \* \* \*